(12) United States Patent
Ji et al.

(10) Patent No.: US 7,867,978 B2
(45) Date of Patent: Jan. 11, 2011

(54) METHODS AND COMPOSITIONS FOR TREATING NEUROLOGICAL DISORDERS

(75) Inventors: Tae H Ji, Lexington, KY (US); Inhae Ji, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 310 days.

(21) Appl. No.: 11/627,005

(22) Filed: Jan. 25, 2007

(65) Prior Publication Data

US 2008/0182784 A1    Jul. 31, 2008

(51) Int. Cl.
*A61K 38/16* (2006.01)

(52) U.S. Cl. .................. 514/17.7; 514/21.3; 530/324

(58) Field of Classification Search ................ None
See application file for complete search history.

(56) References Cited

PUBLICATIONS

Rudinger. In Peptide Hormones. J.A. Parsons, ed. University Park Press, Baltimore, 1976, pp. 1-7.*
Ratovitski et al., JBC, vol. 274, No. 2, Jan. 8, 1999, pp. 993-999.*

* cited by examiner

*Primary Examiner*—Daniel E Kolker
*Assistant Examiner*—Stephen Gucker
(74) *Attorney, Agent, or Firm*—Crowell & Moring LLP

(57) ABSTRACT

This disclosure relates to methods and compositions useful for the treatment of senile dementia. More particularly the disclosure relates to methods and compositions for the treatment of senile dementia related to diabetes.

3 Claims, 7 Drawing Sheets

Human Kalirin genomic DNA(Homo sapiens chromosome 3 genomic conting ; gi NT_005612 Region: 30198024..30638214)

```
-2000                gtact ttgtgaacga aaaagtactg gccacatgtg agcgatggat tcttgttact cgtgaaggga gaaacaccgg gttacttctc
-1915 tctggaggga ggaggagggg tttgcattct tgtgttaact acacactgga gtcttgtcca tttaaggtaa taagaaaata atgctaacag agcctgagag
-1815 gtagcttctt gggtggtgat gtctctgccg agacccaatg ctgccgttta agaagaaacc acaaggcagt tgggggcag gggcaggcgg tggaggttgt
-1715 gactctgctt gctttctccc tctccctcct tgctcctacc ccctggacgt gcctcctccc cagtctgagt tcttcagaaa tctgcaccct ctctcatctt
-1615 ggaggtataa gttccaagga agagctggtg ctgagggaga catgcctcca gttgcctgat ggagaccagg aggcctggga gaccaccatt ctgttaggac
-1515 agtgagaagg cattgctggc atggcctagg ctgcacagag ctgtgatgaa tgtgcagatg gctgttgggt agttttttagg cttggagaac aaggtcatcc
-1415 tagacctggg gactcctcag gtttcatttc agtgaatagc actcccagtc acctgggtca caggctggcc cactgtaaga ggggctgtga ttgggcaagg
-1315 actgggcacc ccgtcatgcc ccaaaggcct tagacaatgc ccaggggctg aggtctctgc agcttacttt tctccttgcc ttgaaaataa cattgtatca
-1215 gggactcaga tgccttgca tgttcatttg tctagttagt aatcactcga gtaactcga agttcagggt tctttgaggg acacaaagat ggagtttatg
-1115 ggcaagtaag ggagaagagt catatacaaa ggagaaggtg gaatgaaaaa aataaaatat aaaggaagga agatcaggga agtctgcctg gattctgtgg
-1015 catttgagtt atttgttgga aaaattaggc ggatttggcc atgatgaggt ggagagtggg gagagcatcc tattgcagg aagggcagga gcaaagtcct
 -915 ggggatagaa aaccgtggga tgtatgaatg tgtggggaac tgagagtctg gcaagaggga gaggggttga gaggtaaggg agaaccttct atctaccagt
 -815 atctaccagg tgcaacacca gaaacattat attcttcttt tgctttgagg ctcacaaata ctgttctctc tggtttacag aggaggaagc tgaggcacat
 -715 ggagctgaaa aacttgatcc aggccaggca agtattaagt ggcaaccagg atttggaccc atgactgtgt gacttcaaag cccatgctgt ctctactata
 -615 acaaaggttc catgaaggga cgtagggaaa aaggatctgt ggccttttac cagtcatgca ggtcctgcag tcttgggcaa ggagagccag tggtccctac
 -515 agtgaggcag tgaggcagta acgctcccag gctcctgac tgcctcaaa gtccaaaatg gcccgagctt tggcttccca tcccatattc tattggagga
 -415 gccactgcc tctggtgtgg gaggtatgga ggccaggatg gcaggagatg ctggaaaaaa tttaagacat ggacttgact gtggattttc attctcaaga
 -315 ccactgcaaa cctcgcgtct ttgcgaaaac ccttcctgac tccctcccac gcatctccga cctcccttg ggtccaggca ggctcggtct gcacacgcg
 -215 ttgttctgca cttgttcctt tgttgctgtg aaaccggctc ccggcacagt cagcctctgt gtgggaggac tggtggctgt cttttgcaggc aggcatttgc
 -115 ttagagcagg ctgtgtgcga gcccagcgtc aagtgattcc ggcctcctcg agtcagcggt ggtgggatga ggctctgccg aggggactgg ctgtgaagga
+1
  -15 tgagttcagg gtgggatgac ggaccgcttc tgggaccagt ggtatctctg gtatctccgc ttgctccggc tgctggatcg ag
```

FIGURE 8

SEQUENCE LISTING

<160> NUMBER OF SEQ ID NOS: 52

<210> SEQ ID NO 1
<211> LENGTH: 4992
<212> TYPE: DNA
<213> ORGANISM: Homo sapiens

<400> SEQUENCE: 1

| | | | | | |
|---|---|---|---|---|---|
| atgacggacc | gcttctggga | ccagtggtat | ctctggtatc | tccgcttgct | ccggctgctg | 60 |
| gatcgagggt | cttttcggaa | tgatggtttg | aaagcttctg | atgtccttcc | tatcctaaag | 120 |
| gaaaaggtgg | ccttcgtgtc | tggggtcgt | gataagcgag | gcggacccat | cctgaccttc | 180 |
| cctgctcgca | gcaatcatga | cagaataaga | caggaagacc | tgcggaaact | cgtgacgtat | 240 |
| ttggccagcg | tgccaagtga | ggacgtgtgc | aaacgtggct | tcactgtcat | catcgacatg | 300 |
| cggggctcca | agtgggacct | catcaagccc | ctcctcaaaa | cgctgcagga | agcctttcca | 360 |
| gctgagatcc | atgtggccct | catcattaaa | cccgacaact | tctggcagaa | acagaagacc | 420 |
| aactttggca | gctccaaatt | catctttgag | acgagcatgg | tatctgtgga | gggcctcaca | 480 |
| aagctggtgg | acccctccca | gctgacggag | gagtttgatg | gctccctgga | ctacaaccat | 540 |
| gaggagtgga | tcgaactgcg | gctctccctg | gaggagttct | caacagcgc | cgtgcacctg | 600 |
| ctctcgcgcc | tcgaggacct | caggagatg | ctagcccgga | aggagtttcc | tgtggatgtg | 660 |
| gagggctctc | ggcggctcat | tgacgaacac | acacagctca | agaaaaaggt | gctgaaggcc | 720 |
| cctgtggagg | agctggaccg | ggaggggcag | cggctgctgc | agtgcatccg | ctgcagcgac | 780 |
| ggcttctcag | gacgcaactg | catcccgggc | agtgctgact | ccagagcct | ggtgcccaag | 840 |
| atcaccagtc | tcctggacaa | gctgcactcc | acccggcagc | acctgcacca | gatgtggcac | 900 |
| gtgcgcaagc | tcaagctgga | ccagtgcttt | cagctgcggc | tcttcgagca | ggatgctgag | 960 |
| aagatgtttg | actggataag | ccacaacaag | gagttattcc | tccagagcca | cacggagatc | 1020 |
| ggagtcagct | accagtacgc | ccttgacctc | cagacgcagc | acaatcactt | tgccatgaac | 1080 |
| tccatgaatg | cctatgtcaa | catcaaccgc | atcatgtccg | tggcttcccg | cctctctgag | 1140 |
| gccggtcatt | atgcctcaca | acaaatcaag | cagatctcca | cccagctgga | ccaggagtgg | 1200 |
| aagagctttg | ctgctgccct | ggatgaacgc | agcaccatcc | tcgccatgtc | tgctgtgttc | 1260 |
| caccagaagg | ctgagcagtt | cctgtcggga | gtggatgcct | ggtgcaagat | gtgcagtgaa | 1320 |
| ggtggtctgc | catccgagat | gcaagaccta | gagctggcaa | tccaccacca | ccagaccttg | 1380 |
| tatgagcagg | tgacccaagc | ctacacagag | gtcagccagg | atggcaaagc | actacttgat | 1440 |
| gtgctgcagc | ggcccctgag | ccctgggaac | tccgaatccc | tcacgccac | agccaactac | 1500 |
| tccaaggcag | tgcaccaggt | gctggacgtg | gtgcatgagg | tgttacatca | ccagcgacgg | 1560 |
| ctggagagca | tctggcagca | ccgcaaggtg | cggctccacc | agcggctgca | gctctgcgtc | 1620 |
| ttccagcagg | atgtacagca | ggtgttggac | tggattgaaa | accatggtga | ggcctttctc | 1680 |
| agcaaacaca | ctggagttgg | gaagtcccta | catcgagccc | gggccctgca | gaagaggcat | 1740 |
| gatgactttg | aagaggtggc | tcagaatacg | taccaccaatg | cggacaagct | cctagaagca | 1800 |
| gcagagcagt | ggctcagac | gggggaatgt | gaccccgagg | agatctacaa | ggcagctcga | 1860 |
| cacctggagg | tgcgcatcca | agacttcgtg | cgcagggtgg | agcagcggaa | gcttctcctg | 1920 |
| gacatgtctt | tttccttcca | cacacacacc | aaagagttgt | ggacatggat | ggaagaccttt | 1980 |
| cagaaggaga | tgttggagga | tgtctgtgca | gattctgtgg | atgcagtcca | ggaactgatc | 2040 |

```
aaacagttcc agcagcagca gaccgccact ctagatgcca cactcaatgt catcaaggaa    2100
ggcgaagacc ttatccagca gctcaggtca gcgcctccct ccctcgggga gcccagcgag    2160
gccagggact cggctgtgtc caacaacaaa acaccccaca gcagctccat cagccacatc    2220
gagtcggtcc tgcagcagct tgatgatgcc caggtgcaga tggaggagct gttccacgag    2280
cggaagatca agctggacat cttcctgcaa ctgcgcatct ttgagcagta caccatcgag    2340
gtgacagcag agctagacgc ctggaatgaa gacttgcttc ggcagatgaa tgacttcaac    2400
acagaggacc taaccctggc agaacagcgg ctgcagcgcc acacagaacg gaagctagcc    2460
atgaacaaca tgacctttga ggttatccag cagggacagg atctgcacca gtacatcacg    2520
gaggtccagg catcaggaat tgagttgatc tgtgaaaaag acattgatct ggcagcccag    2580
gtgcaagagt tattggaatt tctccatgag aagcagcatg aattggagct caatgcagag    2640
cagactcata agcggctaga gcagtgcctc caattacgtc acctccaggc tgaagtcaaa    2700
caggttctgg gatggatccg caatggagag tcaatgctca acgccagcct ggtcaatgcc    2760
agctctttgt cggaagcaga gcagctgcag cgggagcacg agcagttcca actggccatc    2820
gagtccctct tcatgccac ttccttgcag aagacgcacc agagtgccct gcaggtacag    2880
cagaaagccg aggtgctgct ccaggccggc cactacgatg ccgatgccat ccggaatgt    2940
gctgagaagg tggccctcca ctggcagcag ctcatgctga agatggaaga ccggctaaaa    3000
ttggtcaatg cctctgtggc cttttacaaa acttctgaac aggtgtgtag tgtcctggag    3060
agcttagagc aagaataccg gagagatgag gactggtgtg gtggacgaga taagctgggg    3120
ccagcagcag agatcgacca tgtcattccc ctcatcagca acatttgga acaaaaggag    3180
gcctttctta aggcctgcac cctggctcgg cggaatgctg aggtgtttct caagtacatc    3240
cacaggaaca acgtcagcat gcccagtgtc gccagccaca ctcggggacc cgagcaacaa    3300
gtgaaagcca tcctgagtga gctcctgcag agggagaatc gcgtgctgca tttctggacc    3360
ttgaagaagc ggcggttaga ccaatgccag caatatgtgg tgttcgagcg cagcgctaag    3420
caggcgcttg actggatcca agaaacaggt gaatttttacc tctcaacaca tacctccact    3480
ggagagacca cagaggagac tcaggaactg ctgaaagaat atggggaatt cagggtgcct    3540
gccaagcaaa caaaggagaa ggtgaagctt ctgattcagc tggccgatag ctttgtggaa    3600
aaaggccaca ttcatgccac ggagataagg aaatgggtga ccacggtgga caagcactac    3660
agagatttct ccctgaggat gggaaagtac cgatactcac tggagaaagc cctaggagtc    3720
aacacagagg ataataagga cctggagctg atattatcc cagcaagcct ttcggatcgg    3780
gaggtcaagc tgcgggacgc caaccacgaa gtcaatgaag agaagcggaa gtcagcccgg    3840
aagaaagaat ttattatggc tgaactactc cagacagaga aggcttatgt aagggatttg    3900
catgagtgct tagagaccta cctgtgggaa atgaccagtg tgtggagga atcccccct    3960
gggatcctca ataaagagca tatcatcttt ggcaacatcc aagagatcta cgatttccat    4020
aacaacatct tcctcaaaga gctggagaag tacgagcaac tgcctgagga tgtgggacac    4080
tgctttgtta cctgggcaga caaatttcag atgtatgtca cctactgtaa aaacaagcct    4140
gattccaacc agcttatcct ggagcatgcg ggcaccttct ttgatgagat acaacagcgg    4200
catggtctgg ccaactccat ctcttcctac ctaattaagc ctgtccaaag gatcaccaaa    4260
tatcaactgc tcctgaagga acttttaact tgctgtgaag aagggaaagg ggagctcaag    4320
gatggcctgg aggtgatgct cagtgtccca aagaaagcca atgatgccat gcatgtcagc    4380
```

```
atgctggaag ggttcgacga gaacctggat gtgcagggg agttgattct ccaggatgcc    4440
tttcaagtgt gggacccgaa gtcgctgatc cggaagggc gggagcggca cttgttcctc    4500
tttgagatct ccttggtttt tagcaaggag atcaaagatt cttcaggaca cacgaaatat    4560
gtttacaaga acaagctact gacctcagag ctgggtgtga ccgagcacgt ggagggcgat    4620
ccctgcaaat cgccttgtg gtctgggcgc accccatcct cagacaataa aacagtgctg    4680
aaagcctcca acattgaaac caagcaggag tggatcaaga acattcgaga agtgattcaa    4740
gaaaggatca ttcacctgaa aggagcttta aggagccac ttcagctccc caaaacacca    4800
gccaaacaga ggaacaatag taagagggat ggagtggagg atattgacag ccaggggat    4860 gggagcagcc aaccagacac catctccatt gcttctagga cctctcagaa cacagtggac    4920
agtgacaagg atggcaacct tgttcctcgg tggcacctgg acctggaga tcctttctcc    4980 acttacgttt ag                                                       4992
```

<210> SEQ ID NO 2
<211> LENGTH: 1663
<212> TYPE: PRT
<213> ORGANISM: Homo sapiens

<400> SEQUENCE: 2

```
Met Thr Asp Arg Phe Trp Asp Gln Trp Tyr Leu Trp Tyr Leu Arg Leu
  1               5                  10                  15

Leu Arg Leu Leu Asp Arg Gly Ser Phe Arg Asn Asp Gly Leu Lys Ala
                 20                  25                  30

Ser Asp Val Leu Pro Ile Leu Lys Glu Lys Val Ala Phe Val Ser Gly
             35                  40                  45

Gly Arg Asp Lys Arg Gly Gly Pro Ile Leu Thr Phe Pro Ala Arg Ser
         50                  55                  60

Asn His Asp Arg Ile Arg Gln Glu Asp Leu Arg Lys Leu Val Thr Tyr
 65                  70                  75                  80

Leu Ala Ser Val Pro Ser Glu Asp Val Cys Lys Arg Gly Phe Thr Val
                 85                  90                  95

Ile Ile Asp Met Arg Gly Ser Lys Trp Asp Leu Ile Lys Pro Leu Leu
            100                 105                 110

Lys Thr Leu Gln Glu Ala Phe Pro Ala Glu Ile His Val Ala Leu Ile
        115                 120                 125

Ile Lys Pro Asp Asn Phe Trp Gln Lys Gln Lys Thr Asn Phe Gly Ser
    130                 135                 140

Ser Lys Phe Ile Phe Glu Thr Ser Met Val Ser Val Glu Gly Leu Thr
145                 150                 155                 160

Lys Leu Val Asp Pro Ser Gln Leu Thr Glu Glu Phe Asp Gly Ser Leu
                165                 170                 175

Asp Tyr Asn His Glu Glu Trp Ile Glu Leu Arg Leu Ser Leu Glu Glu
            180                 185                 190

Phe Phe Asn Ser Ala Val His Leu Leu Ser Arg Leu Glu Asp Leu Gln
        195                 200                 205

Glu Met Leu Ala Arg Lys Glu Phe Pro Val Asp Val Glu Gly Ser Arg
    210                 215                 220

Arg Leu Ile Asp Glu His Thr Gln Leu Lys Lys Val Leu Lys Ala
225                 230                 235                 240

Pro Val Glu Glu Leu Asp Arg Glu Gly Gln Arg Leu Leu Gln Cys Ile
                245                 250                 255

Arg Cys Ser Asp Gly Phe Ser Gly Arg Asn Cys Ile Pro Gly Ser Ala
```

```
                    260                 265                 270
Asp Phe Gln Ser Leu Val Pro Lys Ile Thr Ser Leu Leu Asp Lys Leu
                275                 280                 285

His Ser Thr Arg Gln His Leu His Gln Met Trp His Val Arg Lys Leu
            290                 295                 300

Lys Leu Asp Gln Cys Phe Gln Leu Arg Leu Phe Glu Gln Asp Ala Glu
305                 310                 315                 320

Lys Met Phe Asp Trp Ile Ser His Asn Lys Glu Leu Phe Leu Gln Ser
                    325                 330                 335

His Thr Glu Ile Gly Val Ser Tyr Gln Tyr Ala Leu Asp Leu Gln Thr
                340                 345                 350

Gln His Asn His Phe Ala Met Asn Ser Met Asn Ala Tyr Val Asn Ile
            355                 360                 365

Asn Arg Ile Met Ser Val Ala Ser Arg Leu Ser Glu Ala Gly His Tyr
        370                 375                 380

Ala Ser Gln Gln Ile Lys Gln Ile Ser Thr Gln Leu Asp Gln Glu Trp
385                 390                 395                 400

Lys Ser Phe Ala Ala Ala Leu Asp Glu Arg Ser Thr Ile Leu Ala Met
                    405                 410                 415

Ser Ala Val Phe His Gln Lys Ala Glu Gln Phe Leu Ser Gly Val Asp
                420                 425                 430

Ala Trp Cys Lys Met Cys Ser Glu Gly Gly Leu Pro Ser Glu Met Gln
            435                 440                 445

Asp Leu Glu Leu Ala Ile His His Gln Thr Leu Tyr Glu Gln Val
        450                 455                 460

Thr Gln Ala Tyr Thr Glu Val Ser Gln Asp Gly Lys Ala Leu Leu Asp
465                 470                 475                 480

Val Leu Gln Arg Pro Leu Ser Pro Gly Asn Ser Glu Ser Leu Thr Ala
                    485                 490                 495

Thr Ala Asn Tyr Ser Lys Ala Val His Gln Val Leu Asp Val Val His
                500                 505                 510

Glu Val Leu His His Gln Arg Arg Leu Glu Ser Ile Trp Gln His Arg
            515                 520                 525

Lys Val Arg Leu His Gln Arg Leu Gln Leu Cys Val Phe Gln Gln Asp
        530                 535                 540

Val Gln Gln Val Leu Asp Trp Ile Glu Asn His Gly Glu Ala Phe Leu
545                 550                 555                 560

Ser Lys His Thr Gly Val Gly Lys Ser Leu His Arg Ala Arg Ala Leu
                    565                 570                 575

Gln Lys Arg His Asp Asp Phe Glu Glu Val Ala Gln Asn Thr Tyr Thr
                580                 585                 590

Asn Ala Asp Lys Leu Leu Glu Ala Ala Glu Gln Leu Ala Gln Thr Gly
            595                 600                 605

Glu Cys Asp Pro Glu Glu Ile Tyr Lys Ala Ala Arg His Leu Glu Val
        610                 615                 620

Arg Ile Gln Asp Phe Val Arg Arg Val Glu Gln Arg Lys Leu Leu Leu
625                 630                 635                 640

Asp Met Ser Val Ser Phe His Thr His Thr Lys Glu Leu Trp Thr Trp
                    645                 650                 655

Met Glu Asp Leu Gln Lys Glu Met Leu Glu Asp Val Cys Ala Asp Ser
                660                 665                 670

Val Asp Ala Val Gln Glu Leu Ile Lys Gln Phe Gln Gln Gln Gln Thr
            675                 680                 685
```

```
Ala Thr Leu Asp Ala Thr Leu Asn Val Ile Lys Glu Gly Glu Asp Leu
        690                 695                 700

Ile Gln Gln Leu Arg Ser Ala Pro Pro Ser Leu Gly Glu Pro Ser Glu
705                 710                 715                 720

Ala Arg Asp Ser Ala Val Ser Asn Asn Lys Thr Pro His Ser Ser Ser
                725                 730                 735

Ile Ser His Ile Glu Ser Val Leu Gln Gln Leu Asp Asp Ala Gln Val
            740                 745                 750

Gln Met Glu Glu Leu Phe His Glu Arg Lys Ile Lys Leu Asp Ile Phe
        755                 760                 765

Leu Gln Leu Arg Ile Phe Glu Gln Tyr Thr Ile Glu Val Thr Ala Glu
    770                 775                 780

Leu Asp Ala Trp Asn Glu Asp Leu Leu Arg Gln Met Asn Asp Phe Asn
785                 790                 795                 800

Thr Glu Asp Leu Thr Leu Ala Glu Gln Arg Leu Gln Arg His Thr Glu
                805                 810                 815

Arg Lys Leu Ala Met Asn Asn Met Thr Phe Glu Val Ile Gln Gln Gly
            820                 825                 830

Gln Asp Leu His Gln Tyr Ile Thr Glu Val Gln Ala Ser Gly Ile Glu
        835                 840                 845

Leu Ile Cys Glu Lys Asp Ile Asp Leu Ala Ala Gln Val Gln Glu Leu
    850                 855                 860

Leu Glu Phe Leu His Glu Lys Gln His Glu Leu Glu Leu Asn Ala Glu
865                 870                 875                 880

Gln Thr His Lys Arg Leu Glu Gln Cys Leu Gln Leu Arg His Leu Gln
                885                 890                 895

Ala Glu Val Lys Gln Val Leu Gly Trp Ile Arg Asn Gly Glu Ser Met
            900                 905                 910

Leu Asn Ala Ser Leu Val Asn Ala Ser Ser Leu Ser Glu Ala Glu Gln
        915                 920                 925

Leu Gln Arg Glu His Glu Gln Phe Gln Leu Ala Ile Glu Ser Leu Phe
    930                 935                 940

His Ala Thr Ser Leu Gln Lys Thr His Gln Ser Ala Leu Gln Val Gln
945                 950                 955                 960

Gln Lys Ala Glu Val Leu Leu Gln Ala Gly His Tyr Asp Ala Asp Ala
                965                 970                 975

Ile Arg Glu Cys Ala Glu Lys Val Ala Leu His Trp Gln Gln Leu Met
            980                 985                 990

Leu Lys Met Glu Asp Arg Leu Lys Leu Val Asn Ala Ser Val Ala Phe
        995                 1000                1005

Tyr Lys Thr Ser Glu Gln Val Cys Ser Val Leu Glu Ser Leu Glu Gln
    1010                1015                1020

Glu Tyr Arg Arg Asp Glu Asp Trp Cys Gly Gly Arg Asp Lys Leu Gly
1025                1030                1035                1040

Pro Ala Ala Glu Ile Asp His Val Ile Pro Leu Ile Ser Lys His Leu
                1045                1050                1055

Glu Gln Lys Glu Ala Phe Leu Lys Ala Cys Thr Leu Ala Arg Arg Asn
            1060                1065                1070

Ala Glu Val Phe Leu Lys Tyr Ile His Arg Asn Asn Val Ser Met Pro
        1075                1080                1085

Ser Val Ala Ser His Thr Arg Gly Pro Glu Gln Gln Val Lys Ala Ile
    1090                1095                1100
```

-continued

```
Leu Ser Glu Leu Leu Gln Arg Glu Asn Arg Val Leu His Phe Trp Thr
1105                1110                1115                1120

Leu Lys Lys Arg Arg Leu Asp Gln Cys Gln Gln Tyr Val Val Phe Glu
        1125                1130                1135

Arg Ser Ala Lys Gln Ala Leu Asp Trp Ile Gln Glu Thr Gly Glu Phe
            1140                1145                1150

Tyr Leu Ser Thr His Thr Ser Thr Gly Glu Thr Thr Glu Glu Thr Gln
        1155                1160                1165

Glu Leu Leu Lys Glu Tyr Gly Glu Phe Arg Val Pro Ala Lys Gln Thr
    1170                1175                1180

Lys Glu Lys Val Lys Leu Leu Ile Gln Leu Ala Asp Ser Phe Val Glu
1185                1190                1195                1200

Lys Gly His Ile His Ala Thr Glu Ile Arg Lys Trp Val Thr Thr Val
        1205                1210                1215

Asp Lys His Tyr Arg Asp Phe Ser Leu Arg Met Gly Lys Tyr Arg Tyr
        1220                1225                1230

Ser Leu Glu Lys Ala Leu Gly Val Asn Thr Glu Asp Asn Lys Asp Leu
        1235                1240                1245

Glu Leu Asp Ile Ile Pro Ala Ser Leu Ser Asp Arg Glu Val Lys Leu
    1250                1255                1260

Arg Asp Ala Asn His Glu Val Asn Glu Glu Lys Arg Lys Ser Ala Arg
1265                1270                1275                1280

Lys Lys Glu Phe Ile Met Ala Glu Leu Leu Gln Thr Glu Lys Ala Tyr
            1285                1290                1295

Val Arg Asp Leu His Glu Cys Leu Glu Thr Tyr Leu Trp Glu Met Thr
            1300                1305                1310

Ser Gly Val Glu Glu Ile Pro Pro Gly Ile Leu Asn Lys Glu His Ile
        1315                1320                1325

Ile Phe Gly Asn Ile Gln Glu Ile Tyr Asp Phe His Asn Asn Ile Phe
    1330                1335                1340

Leu Lys Glu Leu Glu Lys Tyr Glu Gln Leu Pro Glu Asp Val Gly His
1345                1350                1355                1360

Cys Phe Val Thr Trp Ala Asp Lys Phe Gln Met Tyr Val Thr Tyr Cys
        1365                1370                1375

Lys Asn Lys Pro Asp Ser Asn Gln Leu Ile Leu Glu His Ala Gly Thr
        1380                1385                1390

Phe Phe Asp Glu Ile Gln Gln Arg His Gly Leu Ala Asn Ser Ile Ser
    1395                1400                1405

Ser Tyr Leu Ile Lys Pro Val Gln Arg Ile Thr Lys Tyr Gln Leu Leu
    1410                1415                1420

Leu Lys Glu Leu Leu Thr Cys Cys Glu Glu Gly Lys Gly Glu Leu Lys
1425                1430                1435                1440

Asp Gly Leu Glu Val Met Leu Ser Val Pro Lys Lys Ala Asn Asp Ala
            1445                1450                1455

Met His Val Ser Met Leu Glu Gly Phe Asp Glu Asn Leu Asp Val Gln
        1460                1465                1470

Gly Glu Leu Ile Leu Gln Asp Ala Phe Gln Val Trp Asp Pro Lys Ser
    1475                1480                1485

Leu Ile Arg Lys Gly Arg Glu Arg His Leu Phe Leu Phe Glu Ile Ser
    1490                1495                1500

Leu Val Phe Ser Lys Glu Ile Lys Asp Ser Ser Gly His Thr Lys Tyr
1505                1510                1515                1520

Val Tyr Lys Asn Lys Leu Leu Thr Ser Glu Leu Gly Val Thr Glu His
```

-continued

```
                1525                1530                1535

Val Glu Gly Asp Pro Cys Lys Phe Ala Leu Trp Ser Gly Arg Thr Pro
        1540                1545                1550

Ser Ser Asp Asn Lys Thr Val Leu Lys Ala Ser Asn Ile Glu Thr Lys
    1555                1560                1565

Gln Glu Trp Ile Lys Asn Ile Arg Glu Val Ile Gln Glu Arg Ile Ile
1570                1575                1580

His Leu Lys Gly Ala Leu Lys Glu Pro Leu Gln Leu Pro Lys Thr Pro
1585                1590                1595                1600

Ala Lys Gln Arg Asn Asn Ser Lys Arg Asp Gly Val Glu Asp Ile Asp
        1605                1610                1615

Ser Gln Gly Asp Gly Ser Ser Gln Pro Asp Thr Ile Ser Ile Ala Ser
    1620                1625                1630

Arg Thr Ser Gln Asn Thr Val Asp Ser Asp Lys Asp Gly Asn Leu Val
1635                1640                1645

Pro Arg Trp His Leu Gly Pro Gly Asp Pro Phe Ser Thr Tyr Val
    1650                1655                1660

<210> SEQ ID NO 3
<211> LENGTH: 33
<212> TYPE: PRT
<213> ORGANISM: Homo sapiens

<400> SEQUENCE: 3

Lys Ala Ala Arg His Leu Glu Val Arg Ile Gln Asp Phe Val Arg Arg
 1                5                  10                  15

Val Glu Gln Arg Lys Leu Leu Leu Asp Met Ser Val Ser Phe His Thr
            20                  25                  30

His

<210> SEQ ID NO 4
<211> LENGTH: 33
<212> TYPE: PRT
<213> ORGANISM: Homo sapiens

<400> SEQUENCE: 4

Lys Ala Ala Arg His Leu Glu Val Arg Ile Gln Asp Phe Val Arg Arg
 1                5                  10                  15

Val Glu Gln Arg Lys Leu Leu Leu Asp Met Ser Val Ser Phe His Thr
            20                  25                  30

His

<210> SEQ ID NO 5
<211> LENGTH: 33
<212> TYPE: PRT
<213> ORGANISM: Rattus norvegicus

<400> SEQUENCE: 5

Lys Ala Ala Arg His Leu Glu Val Arg Ile Gln Asp Phe Val Arg Arg
 1                5                  10                  15

Val Glu Gln Arg Lys Leu Leu Leu Asp Met Ser Val Ser Phe His Thr
            20                  25                  30

His

<210> SEQ ID NO 6
<211> LENGTH: 33
<212> TYPE: PRT
<213> ORGANISM: Mus musculus
```

```
<400> SEQUENCE: 6

Lys Ala Ala Arg His Leu Glu Val Arg Ile Gln Asp Phe Val Arg Arg
 1               5                  10                  15

Val Glu Gln Arg Lys Leu Leu Leu Asp Met Ser Val Ser Phe His Thr
            20                  25                  30

His

<210> SEQ ID NO 7
<211> LENGTH: 33
<212> TYPE: PRT
<213> ORGANISM: Canis familiaris

<400> SEQUENCE: 7

Lys Ala Ala Arg His Leu Glu Val Arg Ile Gln Asp Phe Val Arg Arg
 1               5                  10                  15

Val Glu Gln Arg Lys Leu Leu Leu Asp Met Ser Val Ser Phe His Thr
            20                  25                  30

His

<210> SEQ ID NO 8
<211> LENGTH: 33
<212> TYPE: PRT
<213> ORGANISM: Tetraodon nigroviridis

<400> SEQUENCE: 8

Lys Ala Ala Arg His Leu Glu Val Arg Ile Gln Asp Phe Val Arg Arg
 1               5                  10                  15

Val Glu His Arg Lys Leu Leu Leu Asp Met Ser Val Ser Phe His Thr
            20                  25                  30

His

<210> SEQ ID NO 9
<211> LENGTH: 32
<212> TYPE: PRT
<213> ORGANISM: Homo sapiens

<400> SEQUENCE: 9

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Thr His
            20                  25                  30

<210> SEQ ID NO 10
<211> LENGTH: 32
<212> TYPE: PRT
<213> ORGANISM: Pan troglodytes

<400> SEQUENCE: 10

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Thr His
            20                  25                  30

<210> SEQ ID NO 11
<211> LENGTH: 32
<212> TYPE: PRT
<213> ORGANISM: Bos taurus

<400> SEQUENCE: 11
```

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Thr His
            20                  25                  30

<210> SEQ ID NO 12
<211> LENGTH: 32
<212> TYPE: PRT
<213> ORGANISM: Rattus norvegicus

<400> SEQUENCE: 12

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Thr His
            20                  25                  30

<210> SEQ ID NO 13
<211> LENGTH: 32
<212> TYPE: PRT
<213> ORGANISM: Mus musculus

<400> SEQUENCE: 13

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Thr His
            20                  25                  30

<210> SEQ ID NO 14
<211> LENGTH: 32
<212> TYPE: PRT
<213> ORGANISM: Gallus gallus

<400> SEQUENCE: 14

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Thr His
            20                  25                  30

<210> SEQ ID NO 15
<211> LENGTH: 32
<212> TYPE: PRT
<213> ORGANISM: Canis familiaris

<400> SEQUENCE: 15

Ala Ala His Gln Leu Glu Asp Arg Ile Gln Asp Phe Val Arg Arg Val
 1               5                  10                  15

Glu Gln Arg Lys Ile Leu Leu Asp Met Ser Val Ser Phe His Ser His
            20                  25                  30

<210> SEQ ID NO 16
<211> LENGTH: 32
<212> TYPE: PRT
<213> ORGANISM: Danio rerio

<400> SEQUENCE: 16

Ala Ala His Gln Leu Glu Asp Arg Ile Gln Asp Phe Val Arg Arg Val
 1               5                  10                  15

Glu Gln Arg Lys Val Leu Leu Asp Met Ser Val Ala Phe His Thr His
            20                  25                  30

<210> SEQ ID NO 17
<211> LENGTH: 32

```
<212> TYPE: PRT
<213> ORGANISM: Danio rerio

<400> SEQUENCE: 17

Ala His Arg His Leu Glu Val Arg Val Gln Glu Phe Val Arg Val
1               5                   10                  15

Glu Gln Arg Lys Leu Leu Leu Asp Ile Ser Val Ser Phe His Thr His
            20                  25                  30

<210> SEQ ID NO 18
<211> LENGTH: 32
<212> TYPE: PRT
<213> ORGANISM: Tetraodon nigroviridis

<400> SEQUENCE: 18

Ala His Gln His Leu Asp Val Arg Ile Gln Asp Phe Val Arg Val
1               5                   10                  15

Glu Gln Arg Lys Val Leu Leu Asp Met Ser Val Ala Phe His Thr His
            20                  25                  30

<210> SEQ ID NO 19
<211> LENGTH: 32
<212> TYPE: PRT
<213> ORGANISM: Tetraodon nigroviridis

<400> SEQUENCE: 19

Ala His Gln His Leu Asp Val Arg Ile Gln Asp Phe Val Arg Val
1               5                   10                  15

Glu Gln Arg Lys Val Leu Leu Asp Met Ser Val Ala Phe Gln Thr His
            20                  25                  30

<210> SEQ ID NO 20
<211> LENGTH: 32
<212> TYPE: PRT
<213> ORGANISM: Tetraodon nigroviridis

<400> SEQUENCE: 20

Ala Ala Asp His Asp Glu Val Ser Ile Ala Asp Ile Gln Arg Arg Val
1               5                   10                  15

Glu Gln Arg Lys Leu Leu Leu Asp Leu Ala Val Ser Phe Tyr Thr His
            20                  25                  30

<210> SEQ ID NO 21
<211> LENGTH: 31
<212> TYPE: PRT
<213> ORGANISM: Strongylocentrotus purpuratus

<400> SEQUENCE: 21

Ala Arg Glu Leu Glu Ala Lys Val Gly Asp Phe Ile Ser Arg Val Ala
1               5                   10                  15

Gln Arg Arg Gln Leu Leu Val Met Ser Val Ala Phe His Gln His
            20                  25                  30

<210> SEQ ID NO 22
<211> LENGTH: 31
<212> TYPE: PRT
<213> ORGANISM: Drosophila melanogaster

<400> SEQUENCE: 22

Ala Arg Glu Leu Glu Leu Gln Val Gly Ser Phe Ala Glu Arg Val Glu
1               5                   10                  15

Gln Arg Arg Arg Arg Leu Asp Met Ala Val Ile Phe Tyr Thr His
            20                  25                  30
```

<210> SEQ ID NO 23
<211> LENGTH: 18
<212> TYPE: PRT
<213> ORGANISM: Aspergillus oryzae

<400> SEQUENCE: 23

Asp Phe Val Arg Arg Val Leu Arg Arg Arg Leu Leu Gln Asn Met Ser
 1               5                  10                  15

Gly Ser

<210> SEQ ID NO 24
<211> LENGTH: 15
<212> TYPE: PRT
<213> ORGANISM: Cryptococcus neoformans

<400> SEQUENCE: 24

Val Lys Met Val Glu Gln Arg Lys Leu Leu Leu Asp Phe Asn Val
 1               5                  10                  15

<210> SEQ ID NO 25
<211> LENGTH: 11
<212> TYPE: PRT
<213> ORGANISM: Medicago truncatula

<400> SEQUENCE: 25

Arg Val Glu Gln Val Lys Leu Leu Leu Asp Met
 1               5                  10

<210> SEQ ID NO 26
<211> LENGTH: 12
<212> TYPE: PRT
<213> ORGANISM: Streptomyces tenjimariensis

<400> SEQUENCE: 26

Arg Ile Glu Asp Ile Val Arg Gln Val Glu Gln Arg
 1               5                  10

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: basic amino acid
<220> FEATURE:
<221> NAME/KEY: MOD_RES
<222> LOCATION: (2)..(4)
<223> OTHER INFORMATION: alpha-helix enhancing amino acid
<220> FEATURE:
<221> NAME/KEY: MOD_RES
<222> LOCATION: (5)
<223> OTHER INFORMATION: basic amino acid
<220> FEATURE:
<221> NAME/KEY: MOD_RES
<222> LOCATION: (6)..(7)
<223> OTHER INFORMATION: alpha-helix enhancing amino acid
<220> FEATURE:
<221> NAME/KEY: MOD_RES
<222> LOCATION: (8)
<223> OTHER INFORMATION: basic amino acid

<400> SEQUENCE: 27

Xaa Xaa Xaa Xaa Xaa Xaa Xaa Xaa
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: basic amino acid
<220> FEATURE:
<221> NAME/KEY: MOD_RES
<222> LOCATION: (2)..(3)
<223> OTHER INFORMATION: alpha-helix enhancing amino acid
<220> FEATURE:
<221> NAME/KEY: MOD_RES
<222> LOCATION: (4)..(5)
<223> OTHER INFORMATION: basic amino acid
<220> FEATURE:
<221> NAME/KEY: MOD_RES
<222> LOCATION: (6)..(7)
<223> OTHER INFORMATION: alpha-helix enhancing amino acid
<220> FEATURE:
<221> NAME/KEY: MOD_RES
<222> LOCATION: (8)
<223> OTHER INFORMATION: basic amino acid

<400> SEQUENCE: 28

Xaa Xaa Xaa Xaa Xaa Xaa Xaa Xaa
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Lys Arg Pro Lys Pro Gly
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Arg or Lys
<220> FEATURE:
<221> NAME/KEY: MOD_RES
<222> LOCATION: (4)
<223> OTHER INFORMATION: variable amino acid
<220> FEATURE:
<221> NAME/KEY: MOD_RES
<222> LOCATION: (5)
<223> OTHER INFORMATION: Arg or Lys

<400> SEQUENCE: 30

Lys Xaa Arg Xaa Xaa
 1               5

<210> SEQ ID NO 31

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Lys Lys Arg Arg Gln Arg Arg Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Gly Gly Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Lys Ser Ser Gly Ser Gly Ser Glu Ser Lys Ser
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ser Thr Ser Gly Ser Gly Lys Ser Ser Glu Gly Lys Gly
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Gly Ser Thr Ser Gly Ser Gly Lys Ser Glu Gly Ser Gly Ser Thr
1               5                   10                  15

Lys Gly
```

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Gly Ser Thr Ser Gly Ser Gly Lys Pro Gly Ser Gly Glu Gly Ser Thr
1               5                   10                  15

Lys Gly
```

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Glu Gly Lys Ser Ser Gly Ser Gly Ser Glu Ser Lys Glu Phe
1               5                   10
```

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
catgcgggca ccttctttg                                                19

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gttttattgt ctgaggatgg gg                                            22

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cttcagtatc acaacctcag c                                             21

<210> SEQ ID NO 42
<211> LENGTH: 22
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 42
gatgtgttca aacatttccc gg                                               22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
caacggattt ggtcgtattg g                                                21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagtggactc cacgacgtac t                                                21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tggagagtca atgctcaacg                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtcttctgca aggaagtggc                                                  20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgcaccacca ccaactgctt a                                                21

<210> SEQ ID NO 48
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 48
gaggcaggga tgatgtt                                                    17

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cggaggagac gcgggcac                                                   18

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tcagtgattg tcgctgggca c                                               21

<210> SEQ ID NO 51
<211> LENGTH: 2067
<212> TYPE: DNA
<213> ORGANISM: Homo sapiens

<400> SEQUENCE: 51
gtactttgtg aacgaaaaag tactggccac atgtgagcga tggattcttg ttactcgtga       60
agggagaaac accgggttac ttctctctgg agggaggagg aggggtttgc attcttgtgt      120
taactacaca ctggagtctt gtccatttaa ggtaataaga aaataatgct aacagagcct      180
gagaggtagc ttcttgggtg gtgatgtctc tgccgagacc caatgctgcc gtttaagaag      240
aaaccacaag gcagttgggg ggcaggggca ggcggtggag gttgtgactc tgcttgcttt      300
ctccctctcc ctccttgctc ctaccccctg gacgtgcctc ctcccagtc tgagttcttc       360 agaaatctgc accctctctc atcttggagg tataagttcc aaggaagagc tggtgctgag      420
ggagacatgc ctccagttgc ctgatggaga ccaggaggcc tggagaccca ccattctgtt      480
aggacagtga gaaggcattg ctggcatggc ctaggctgca cagagctgtg atgaatgtgc      540
agatggctgt tgggtagttt ttaggcttgg agaacaaggt catcctagac ctggggactc      600
ctcaggtttc atttcagtga atagcactcc cagtcacctg gtcacaggc tggcccactg       660 taagaggggc tgtgattggg caaggactgg gcaccccgtc atgccccaaa ggccttagac      720
aatgcccagg ggctgaggtc tctgcagctt acttttctcc ttgccttgaa ataacattg      780 tatcagggac tcagatgccc ttgcatgttc atttgtctag ttagtaatca ctcgagtaac      840
tgcgaagttc agggttcttt gagggacaca agatggagt ttatgggcaa gtaagggaga      900
agagtcatat acaaaggaga aggtggaatg aaaaaaataa aatataaagg aaggaagatc      960
agggaagtct gcctggattc tgtggcattt gagttatttg ttggaaaaat taggcggatt     1020
tggccatgat gaggtggaga gtggggagag catcctattg gcaggaaggg caggagcaaa     1080
gtcctgggga tagaaaaccg tgggatgtat gaatgtgtgg ggaactgaga gtctggcaag     1140
```

```
                                    -continued
agggagaggg gttgagaggt aagggagaac cttctatcta ccagtatcta ccaggtgcaa  1200
caccagaaac attatattct tcttttgctt tgaggctcac aaatactgtt ctctctggtt  1260
tacagaggag gaagctgagg cacatggagc tgaaaaactt gatccaggcc aggcaagtat  1320
taagtggcaa ccaggatttg gacccatgac tgtgtgactt caaagcccat gctgtctcta  1380
ctataacaaa ggttccatga agggacgtag ggaaaaagga tctgtggcct tttaccagtc  1440
atgcaggtcc tgcagtcttg ggcaaggaga gccagtggtc cctacagtga ggcagtgagg  1500
cagtaacgct cccaggctcc tggactggcc tcaaagtcca aaatggccga gcttctggct  1560
tcccatccca tattctattg gaggagccac tggcctctgg tgtgggaggt atggaggcca  1620
ggatggcagg agatgctgga aaaaatttaa gacatggact tgactgtgga ttttcattct  1680
caagaccact gcaaacctcg cgtctttgcg aaaaccctct ctgactccct cccacgcatc  1740
tccgacctcc ccttgggtcc aggcaggctc ggtctgcaca cggcgttgtt ctgcacttgt  1800
tcctttgttg ctgtgaaacc ggctcccggc acagtcagcc tctgtgtggg aggactggtg  1860
gctgtctttg caggcaggca tttgcttaga gcaggctgtg tgcgagccca gcgtcaagtg  1920
attccggcct cctcgagtca gcggtggtgg gatgaggctc tgccgagggg actggctgtg  1980
aaggatgagt tcagggtggg atgacggacc gcttctggga ccagtggtat ctctggtatc  2040
tccgcttgct ccggctgctg gatcgag                                     2067
```

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 52

His His His His His His
 1               5

METHODS AND COMPOSITIONS FOR TREATING NEUROLOGICAL DISORDERS

STATEMENT REGARDING FEDERALLY SPONSORED RESEARCH

This invention was supported in part by Grant Nos. RO1 HD18702 and RO1 GM74101 and 5P50AG05144 awarded by the National Institutes of Health. The government may have certain rights in this invention.

TECHNICAL FIELD

This disclosure relates to methods and compositions useful for the treatment of dementia. More particularly the disclosure relates to methods and compositions for the treatment of neurodegenerative diseases and disorders including senile dementia and Alzheimer's Disease (AD).

BACKGROUND

Nitric oxide synthase (NOS) is an enzyme which is found in humans. Three isoforms of NOS have been identified. In the body nNOS and eNOS are constitutively expressed in the cells in which they are found. However, iNOS is not constitutively expressed, but is known to be induced by a number of cytokines, lipopolysaccarides (LPS), and other mediators of the inflammatory response. Specifically, iNOS has been associated as indicating certain pathological disease states.

Alzheimer's disease (AD) is the major cause of dementia in the elderly. Although rare genetic forms of AD exist, most patients are classified as having sporadic AD, since no family history is usually identified. Pathologically, AD is characterized by neuronal and synaptic degeneration with an increased number of senile plaques and neurofibrillary tangles compared to non-demented individuals of comparable age.

The senile plaques, characteristic of Alzheimer's disease, are composed of a central core of aggregated beta-amyloid, a breakdown product of amyloid precursor protein (APP). The neurofibrillary tangles are insoluble intracellular thread-like structures made up of a hyperphosphorylated form of a protein called tau, which is associated with microtubles.

Early and accurate diagnosis of Alzheimer's disease is important since early intervention may delay or arrest the reversible neuronal damage. Clinical diagnosis is not always accurate since the criteria are relatively subjective and the disease needs to be differentiated from other dementing illnesses.

SUMMARY

The invention provides a method for diagnosing and monitoring senile dementia or other neurodegenerative disease or disorder in a subject comprising detecting a kalirin polypeptide or polynucleotide in a sample derived from the subject, wherein a reduction or mutation in kalirin is indicative of the onset, progress or late stage of dementia.

The invention also provides a method for determine a subject's risk for senile dementia comprising: (a) obtaining a sample derived from a subject; (b) detecting or identifying in the sample a kalirin polypeptide or polynucleotide; and (c) comparing the detected amount with an amount detected for a normal control, wherein a reduction in kalirin is indicative or a risk of senile dementia.

The invention further provides a method for suppressing the induction of inducible nitric oxide synthase in a cell comprising contacting said cell with an effective amount of at least one induction suppressor of inducible nitric oxide synthase, wherein said induction suppressor is selected from the group consisting of a kalirin polynucleotide or oligonucleotide, a kalirin polypeptide, and/or an active fragment of a kalirin polypeptide.

The invention provides a method of inhibiting nitric oxide cytotoxicity comprising contacting a cell capable of producing nitric oxide with a biologically effective amount of an agent comprising a kalirin polynucleotide, a kalirin polypeptide, an active fragment of a kalirin polypeptide and/or a kalirin agonist that regulates inducible nitric oxide synthase under conditions wherein the agent reduces inducible nitric oxide synthase activity.

The invention provides a composition comprising an active fragment of kalirin in a pharmaceutically acceptable carrier.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8 shows the upstream regulatory sequence (SEQ ID NO:51) of kalirin 7.

DETAILED DESCRIPTION

As used herein and in the appended claims, the singular forms "a," "and," and "the" include plural referents unless the context clearly dictates otherwise. Thus, for example, reference to "a protein" includes a plurality of such proteins and reference to "the cell" includes reference to one or more cells known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Alzheimer's disease (AD) is the most prevalent adult dementing disorder. The pathological characteristics of AD are brain atrophy, amyloid plaques and neurofibrillary tangle formation, and neuron and synapse loss. AD is related to a number of factors including the presence of amyloid-β peptide, presenilins 1 and 2, NO and iNOS production and activity (respectively), and apolipoprotein E (ApoE) isoforms, impacting gene expression in AD. The gene expression analysis provided herein of hippocampal and cerebellar specimens of 19 AD in comparison to 15 age- and sex-matched control brains shows many AD-associated differentially expressed genes and expressed sequence tags. Among them is the gene Kalirin, specifically the Kalirin-7 isoform.

Figure 3:
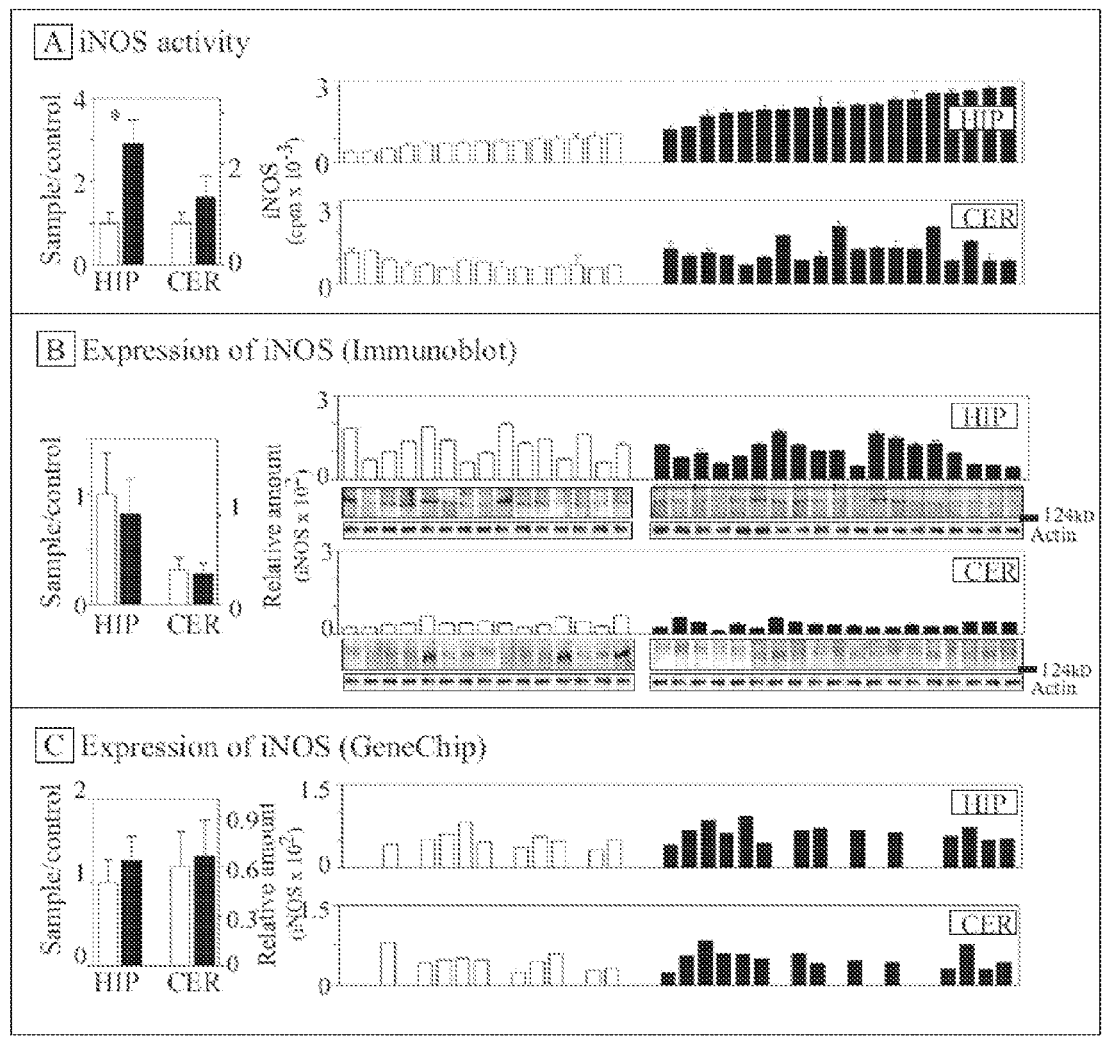
FIG. 3A-C shows activity and expression of iNOS. (A) The average activities of iNOS for control (open bar) and AD (black bar) hippocampi (HIP) and cerebella (CER). The left side Y axis represents the ratio of AD/control value, and the right side Y axis represents the actual value. The means (bars) and standard deviations (error bars) are presented. The samples with statistically significant differences between AD and control are marked as (*) for $p<0.0001$ and (+) for $0.05<P>0.0001$. HIP=hippocampus and CER=cerebellum. (HIP) The iNOS activity of individual control (open bar) and AD (black bar) hippocampi. The samples were sorted in the order of increasing iNOS activity. (CER) The iNOS activity of individual cerebella as described above. (B) The average concentration of immunoblotted iNOS of hippocampi and cerebella. (HIP) Immunoblotted iNOS (upper blots) and actin (lower blots) concentrations of individual hippocampi. (CER) Immunoblotted iNOS (upper blots) and actin (lower blots) concentrations of individual cerebella. (C). The average amount of iNOS mRNA expression determined by Affymetrix U133A chip. (HIP) iNOS mRNA concentration of individual hippocampi. (CER) iNOS mRNA concentration of individual cerebella.
Figure 7:
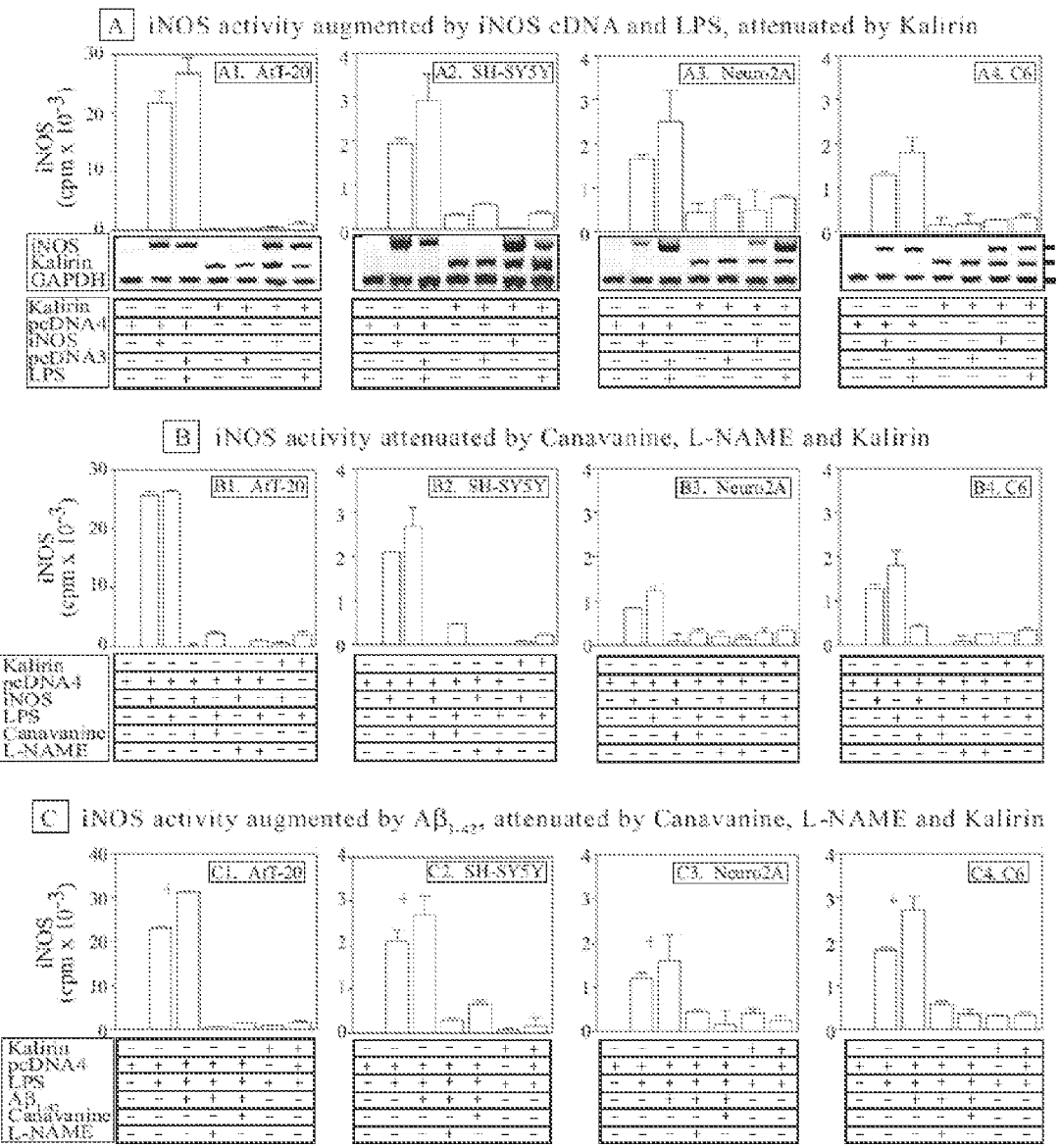
FIG. 7A-C shows induction and attenuation of iNOS by LPS (A-C), iNOS plasmid (A-C) and A β1-42 (C), and attenuation of iNOS by Kalirin (A-C) and inhibitors of NOS (B, C). (A) Induction of iNOS by LPS and iNOS plasmid and attenuation of iNOS by Kalirin in mouse AtT20, human neuroblastoma SH-SY5Y cell line, mouse neuroblastoma Neuro2A cell line, and rat glioma C6 cell line. The cell lines were stably transfected either with pcDNA4 carrying the Kalirin-7 cDNA (denoted as Kalirin) or with empty pcDNA4. The two types of stable cell lines were established and transiently transfected either with pcDNA3 carrying the iNOS cDNA (denoted as iNOS) or empty pcDNA3. Some of the cells were also treated with LPS for 16 h to induce iNOS. In addition, RNAs were extracted from the cells and used to produce the cDNA fragments for iNOS, Kalirin and GAPDH by RT-PCR as shown underneath the bar graph. (B) Attenuation iNOS by NOS inhibitors. The stable cell lines described in A were assayed for iNOS with or without a specific inhibitor for iNOS (Canavanine) or general inhibitor for NOS (L-NAME). (C) Effect of Aβ1-42. Stable cell lines described in A were treated with LPS plus Aβ1-42 for 16 h and assayed for iNOS.

Inducible nitric oxide (iNOS) and NO have been shown to be important in AD. High iNOS activity cannot be explained by the expression levels of iNOS mRNA and protein in AD and control hippocampi. For example, iNOS knockout mice are protected from the AD phenotype. Amyloid-β induces iNOS activity and elevated NO levels are globally observed in AD hippocampi compared to normal tissues. However, iNOS protein expression and its enzymatic activity do not show a correlation (FIGS. 3A and 3B), suggesting that iNOS activity is regulated through a mechanism other than expression levels. The importance of other regulatory mechanism is further underscored by the fact that NO levels vary dramatically among various cell lines (FIG. 7). The iNOS activity is ~10 fold higher in AtT-20 cells than other cell lines described in FIG. 7 and ~100 fold higher than HEK293 cells stably expressing iNOS. The under expression of Kalirin-7 correlate with elevated iNOS activity in AD hippocampi, which is higher in all of the 19 AD hippocampal specimens compared with all of the tissue specimens of the 15 control hippocampi, 19 AD cerebella and 15 control cerebella.

Kalirin-7 is a cytoplasmic protein of >1,660 amino acids and plays crucial regulatory roles in growth and maintenance of neurons. Kalirin comprises over a dozen alternate splicing forms, all primarily expressed in the brain, particularly in the hippocampus with the most intense expression in neurons; tissue culture studies demonstrate that Kalirin isoforms play crucial roles in neuronal stability and growth. Kalirin is essential for the growth and maintenance of hippocampal pyramidal neuron dendrites and dendritic spines. Originally cloned from rat and human brains, Kalirin plays a role in the huntingtin dependent Ras-related signal pathway and pathogenesis of Huntington's disease, an autosomal dominant neurodegenerative disease that is frequently associated with dementia. Kalirin interacts with a number of cytoplasmic proteins, including the cytoplasmic domain of peptidylglycine α-amidating monooxygenase, huntingtin-associated protein 1 and iNOS. However, there are no prior reports demonstrating a direct role for any Kalirin isoform in any neurodegenerative disorders and other diseases. The regulatory effect of the Kalirin domain and Kalirin have therapeutic potential in controlling iNOS activity and thus limit AD development. In addition to Kalirin-7, genes for voltage-gated $Ca^{2+}$ channel γ-subunit 3 and visinin-like protein 1 (a $Ca^{2+}$ sensor protein) are under-expressed, whereas inositol 1,4,5-triphosphate 3-kinase B is over-expressed. Collectively, these differential expression patterns can impair $Ca^{2+}$ homeostasis. In contrast to the differentially expressed genes, housekeeping genes such as ribosomal protein genes are not affected by AD.

Figure 5:
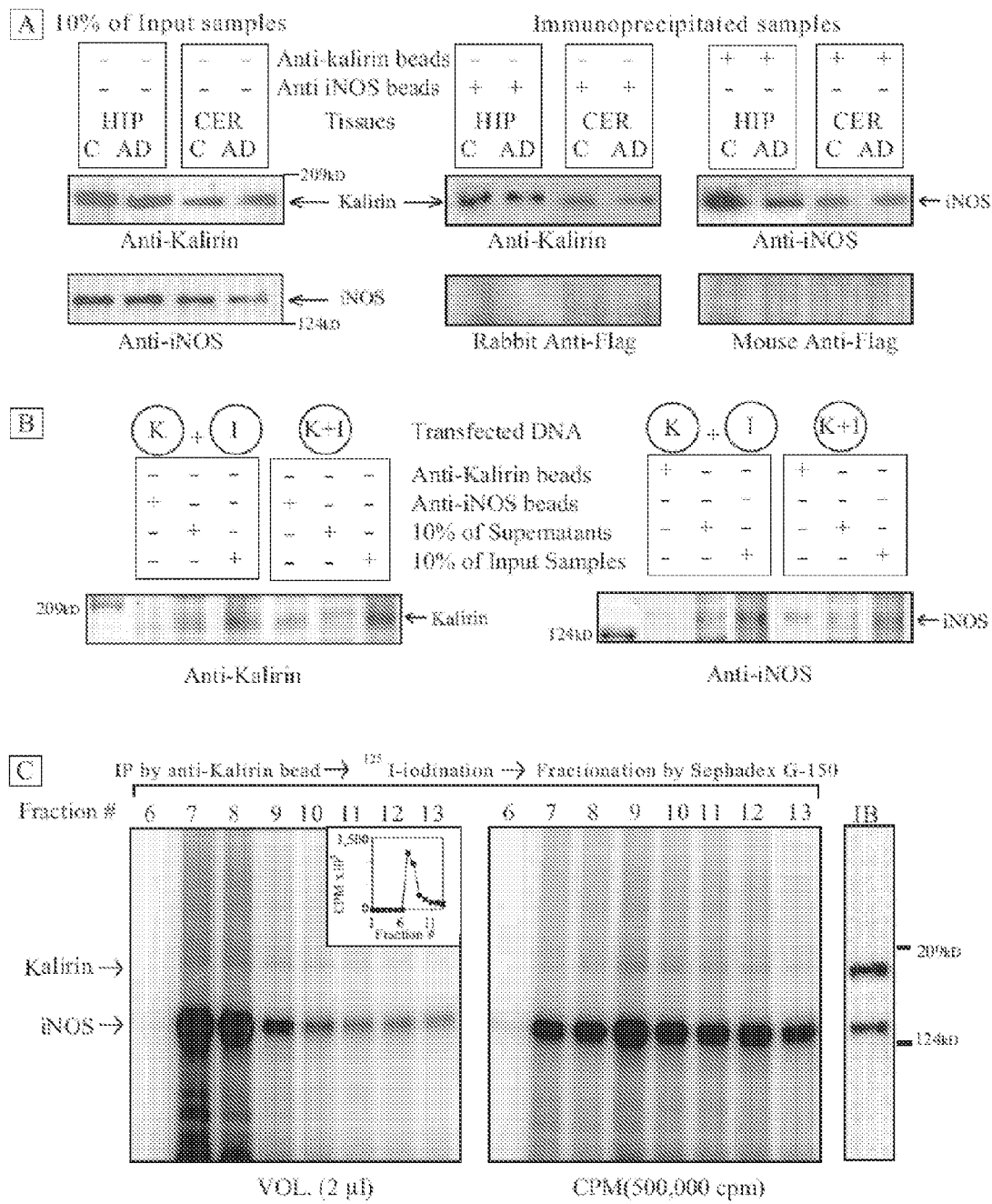
FIG. 5A-C shows co-immunoprecipitation of Kalirin and iNOS. (A) Left Panels: Ten percent of the pooled samples were solubilized and immunoblotted with anti-Kalirin (upper blot) or anti-iNOS (lower blot). Right Panels: The pooled samples were immunoprecipitated with anti-iNOS beads or anti-Kalirin beads and immunoblotted with anti-Kalirin or anti-iNOS, respectively (upper blots). In addition, the blot was probed with rabbit anti-Flag or mouse anti-Flag, respectively, as the negative immunoblot controls (lower blots). (B) Left Panel: The cells expressing Kalirin (K) and the cells expressing iNOS (I) were combined, solubilized, immunoprecipitated with anti-iNOS beads, and immunoblotted with anti-Kalirin. In addition, 10% of the input and 10% of the supernatant of the immunoprecipitation were immunoblotted with anti-Kalirin. When the cells co-expressing both Kalirin and iNOS (KI) were solubilized, immunoprecipitated with anti-iNOS beads, and immunoblotted with anti-Kalirin, Kalirin was immunoprecipitated. Right Panel: The same as described for the Left Panel, except for that the solubilized samples were immunoprecipitated with anti-Kalirin and immunoblotted with anti iNOS. (C) Autoradiogram of anti-Kalirin immunoprecipitate of AD Hippocampus sample. The pooled AD Hippocampal sample was immunoprecipitated with anti-Kalirin and radio-iodinated. Free iodine was removed by fractionation on a Sephadex G-150 column. An equal volume (Left Panel) or equal CPM (Right Panel) of individual tubes was electrophoresed and autoradiographed. The radioactivities of individual tubes were plotted (inset graph of the Left Panel). Immunoblots of Kalirin and iNOS (as shown in A) are combined to show the band positions of Kalirin and iNOS.
Figure 6:
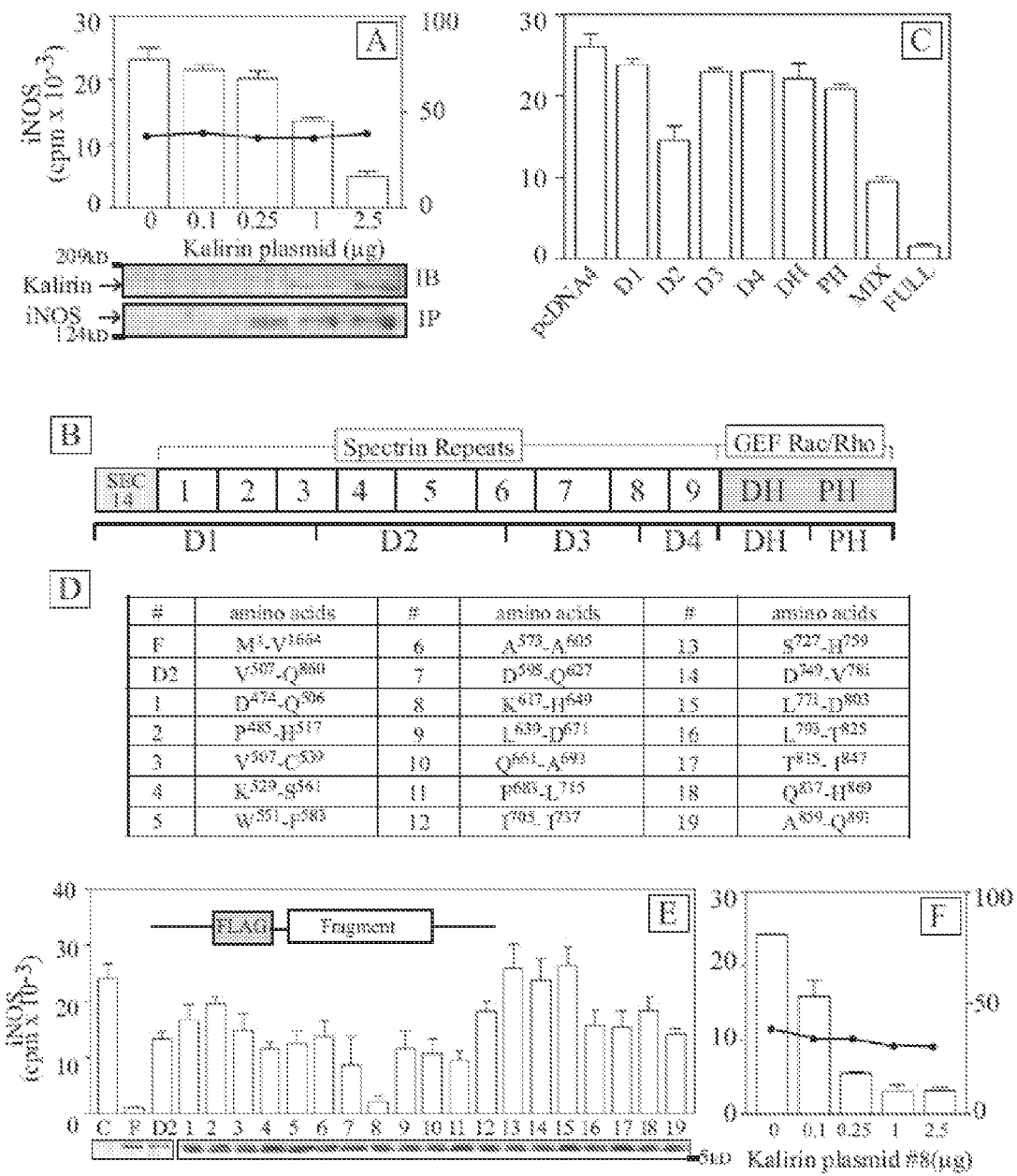
FIG. 6A-F shows identification of Kalirin domain responsible for attenuation of iNOS. (A) Effect of Kalirin plasmid on iNOS. The AtT-20 cell line stably expressing iNOS was transiently transfected with increasing amounts of the pcDNA4 carrying the Kalirin-7 cDNA and assayed for iNOS. The cells were solubilized and 10% of the solubilized samples were immunoblotted with anti-Kalirin (upper gel). The rest of the solubilized samples were immunoprecipitated with anti-Kalirin and immunoblotted with anti-iNOS (lower gel). To test for a potential toxic effect of the Kalirin plasmid on the cells, the cells were transiently co-transfected with increasing amounts of the pcDNA4 carrying Kalirin-7 cDNA plus a constant amount of the pRL-TK vector encoding Renilla luciferase, and assayed for iNOS (bar) and luciferase (dotted line). (B) Kalirin comprises a Sec14p-like putative lipid binding domain, nine spectrin-like repeats, tandem DH and pleckstrin homology (PH) domain. (C) A continuous series of Kalirin domains (D1, D2, D3, D4, DH and PH shown in 5C) was subcloned into pcDNA4. When AtT-20 cells stably expressing iNOS were transiently transfected with various pcDNA4 carrying the individual domains of Kalirin-7, iNOS was most notably attenuated by D2. "Mix" stands for the mixture of the domain plasmids and "Full" stands for the plasmid encoding the full length Kalirin-7. (D) D2 domain was further divided into 19 overlapping sections, each comprising 33 amino acids. The cDNAs for the 19 sections were cloned into pcDNA 4. (E) AtT-20 cell line stably transfected with iNOS was transiently transfected with the pcDNA4 carrying individual Kalirin section cDNAs with the Flag epitope and assayed for iNOS. The activities were compared to the activities of nontransfected cells (C), cells transfected with the full length Kalirin-7 (F) and cells transfected with D2. In addition, the cells were solubilized, and 10% of the solubilized samples were electrophoresed on polyacrylamide gel (7.5% gel for C, F and D2, and 15% gel for sections 1-19) and immunoblotted with anti-Flag (lower panel). The blotted bands of C, F and D2 were aligned to those of sections 1-19 to save space. The 5 kD maker is for the sections 1-19. (F) AtT-20 cell line stably expressing iNOS was transiently transfected with increasing amounts of the pcDNA4 carrying Kalirin section 8 cDNA and assayed for iNOS. The cells were also tested for the toxic effect of the plasmid itself by co-transfecting them with a constant amount of the pRL-TK vector encoding Renilla luciferase as described in (5A). The dotted line represents the luciferase activity. The attempt to immunoblot the cells with anti-Kalirin failed to recognize the Kalirin fragments.

Human Kalirin-7 associates with iNOS in the human hippocampus (FIG. 5) and negatively regulates iNOS enzyme activity in neuronal cell lines (FIG. 7), consistent with the observation that rat Kalirin interacts with mouse iNOS, inhibits the dimerization of iNOS and its activity in the mouse cell system. Furthermore, Kalirin-7 ssociates with inducible NO synthase (iNOS) protein in the human hippocampus and negatively regulates iNOS enzyme activity. The inhibition is attributed primarily to the ~33 amino acid domain around $K^{617}$-$H^{649}$ (SEQ ID NO:3 or SEQ ID NO:2 from amino acid 617 to 649; see FIG. 6), demonstrating that Kalirin 7 is responsible for the negative regulation of iNOS. These results indicate that the elevated NO level in the AD hippocampal specimens is closely correlated with the enhanced iNOS activity and to the under-expression of Kalirin-7. It also provides a simple explanation for the correlation of the low level of neuronal Kalirin and the high activity of iNOS in AD (FIGS. 2 and 3A) that is expressed throughout neuronal and non-neuronal cells as well as aberrant NOS expression in AD. Individual specimens show significant variations in the expression levels of NOS, which could have contributed, along with variant locations of small specimens excised from the hippocampus, to diverse observations on aberrant NOS expression in AD.

The disclosure established the under-expression of Kalirin-7 in AD hippocampus and its role in AD that includes the complex formation with iNOS and deleterious NO in AD brain, further damaging the negative regulation of iNOS activity. The data demonstrate that the regulation of Kalirin 7 expression and decrease in Kalirin-7 expression in AD brain activity in the hippocampus contributes to AD development through iNOS and NO production.

The disclosure demonstrates that the most prevalent isoform of Kalirin in the adult brain, Kalirin-7, is significantly diminished in AD patient brains, both at the mRNA and protein levels. The disclosure further demonstrates a complex of Kalirin-7 with iNOS, with less Kalirin-7 being consumed in this complex with iNOS in AD brain extracts than in control brain extracts. Since the amyloidogenic peptide A β1-42 induces iNOS in brain and Kalirin normally inactivates some iNOS in brain, the data demonstrate that the decrease in Kalirin-7 expression in AD brain contributes to the increased production of deleterious NO in AD brain, further damaging the AD brain.

Accordingly, the disclosure provides methods and compositions for the treatment of dementia caused by decreased kalirin, increased iNOS activity, and increased NO in neurons. Furthermore, the disclosure provides methods of diagnoses and prognoses of dementia.

In one aspect, the disclosure provides a method of alleviating senile dementia (e.g., AD) comprising contacting a subject with an active fragment of kalirin. In one aspect, the senile dementia is associated with elevated levels of NO. In another aspect, the senile dementia is associated with elevated iNOS activity.

The effectiveness of the method of the disclosure in alleviating senile dementia can be demonstrated using recognized animal models of AD as well as in vitro assays that detect changes in iNOS or NO in a biological sample upon exposure to a test agent (e.g., an active fragment of kalirin).

As used herein, the term "inhibiting senile dementia" or "alleviating senile dementia" refers to any diminution in the severity of senile dementia. In a human subject, an active fragment of kalirin or kalirin therapy reduces the severity of senile dementia such that the subject's suffering or dementia (e.g., duration or severity) is diminished and quality of life is improved. Alternatively, the dementia of a subject may be reduced but may not be readily apparent, under these circumstances, a reduction in NO, iNOS or Aβ peptides may be indicative of a reduction in the severity of the disorder.

For use in alleviating senile dementia in a human subject, an active fragment of human kalirin such as, for example, SEQ ID NO:3 is used. However, an active fragment derived from another mammalian kalirin polypeptide is useful in alleviating senile dementia according to the method of the disclosure. Thus, for example, an active fragment of mouse kalirin, rat kalirin, guinea pig kalirin or bovine kalirin can be useful in alleviating senile dementia in a subject. As set forth above, the amino acid sequence of an active fragment of kalirin (SEQ ID NO:3), which corresponds to amino acids 617-649 of kalirin, is well conserved among other species. A peptide useful in the methods of the disclosure can include, for example, SEQ ID NOS:3 through 26 (see TABLE above).

"Dementia" and "senile dementia" refer to a decline in cognitive function due to deterioration of neurons and neuronal signaling beyond what is expected due to normal aging. Cognitive areas that are effected include memory, attention, language and problem solving. An affected persons can be disoriented in time and place. Symptoms of dementia can be classified as either reversible or irreversible depending upon the etiology of the disease. Less than 10% of all dementias are reversible. Senile dementia can be caused by a number of diseases and disorder. For example, senile dementia can be caused by Alzheimer's disease, vascular dementia (also known as multi-infarct dementia), including Binswanger's disease, dementia with Lewy bodies (DLB), Alcohol Induced Persisting Dementia, Frontotemporal lobar degeneration (FTLD), including Pick's disease, Frontotemporal dementia (or frontal variant FTLD), Semantic dementia (or temporal variant FTLD), and progressive non-fluent aphasia, to name a few. In some aspect, the senile dementia can be attributed to the activity of induced nitric oxide synthase (iNOS) and the formation of Aβ secretions. One such pathological conditions associated with Aβ secretions is Alzheimer's Disease (AD).

"Pathological conditions associated with Aβ secretion" include conditions associated with abnormalities in the APP pathway, including but not limited to, modified APP metabolism or processing of components involved in the APP pathway, for example, abnormal α-, β-, or γ-secretase activity, and/or Aβ secretion which may be characterized by the formation of insoluble amyloid deposits (senile plaques), the major component of which is the 40-42 amino acid amyloid beta (Aβ) peptide, a proteolytic product of the amyloid precursor protein (APP). Such conditions include Alzheimer's Disease as well as other conditions characterized by degeneration and eventual death of neurons in brain clusters controlling memory, cognition and behavior. Such conditions may also include, but are not limited to, Parkinson's Disease, tauopathies, prion diseases, frontotemporal dementia, striatonigral degeneration, Lewd body dementia, Huntington's disease, Pick's disease, amyloidosis, and other neurodegenerative disorders associated with excess Aβ production.

A "polynucleotide", as used herein, refers to an oligonucleotide, nucleotide or polynucleotide, and fragments or portions thereof, and to DNA or RNA of genomic or synthetic origin that may be single or double stranded, and represent the sense or antisense strand.

A "cDNA" refers to DNA that is complementary to a portion of messenger RNA (mRNA) sequence and is generally synthesized from an mRNA preparation using reverse transcriptase.

The individual proteins/polypeptides referred to herein include any and all forms of these proteins including, but not limited to, partial forms, isoforms, variants, precursor forms, the full length protein, fusion proteins containing the sequence or fragments of any of the above, from human or any other species. Protein homologs or orthologs which would be apparent to one of skill in the art are included and contemplated by the disclosure. It is also contemplated that the term refers to proteins isolated from naturally occurring sources of any species such as genomic DNA libraries as well as genetically engineered host cells comprising expression systems, or produced by chemical synthesis using, for instance, automated peptide synthesizers or a combination of such methods. Means for isolating and preparing such polypeptides are well understood in the art.

The term "sample" as used herein, is used in its broadest sense. A biological sample from a subject may comprise blood, urine, brain tissue, primary cell lines, immortalized cell lines, or other biological material with which protein activity or gene expression may be assayed. A biological sample may include, for example, blood, tumors or other specimens from which total RNA may be purified for gene expression profiling using, for example, conventional glass chip microarray technologies such as Affymetrix chips, RT-PCR or other conventional methods. In one aspect, a sample comprises cerebral spinal fluid and/or neurological tissue.

A "therapeutically effective amount" is the amount of a polypeptide or polynucleotide of the disclosure sufficient to treat, prevent or ameliorate pathological conditions associated with dementia and/or nitric oxide and/or iNOS production or activity.

A "subject" refers to any human or nonhuman mammal.

The disclosure provides methods and compositions useful in alleviating senile dementia (e.g., AD) resulting from or associated with NO activity or production and/or a reduction in kalirin 7 production or expression.

The method of the disclosure can be useful in alleviating senile dementia regardless of the etiology. For example, a method of the disclosure can be used to alleviate senile dementia resulting from a decrease in kalirin expression, iNOS overexpression, NO production and the like.

An agonist is any molecule that improves the activity of a different molecule; e.g., a hormone, which acts as an agonist when it binds to its receptor, thus triggering a biochemical response, or the production of a heterologous molecule that increase the biological activity in cell. associated with a similar homogenous molecule. For example, a kalirin agonist can be capable of interacting with iNOS.

In one embodiment, a kalirin agonists may be a heterologous kalirin polypeptide or polynucleotide or a kalirin-derived peptide. As used herein, the term "active fragment of kalirin" is synonymous with "kalirin-derived peptide" and "kalirin". A peptide useful in the methods of the disclosure can be derived from kalirin (see, e.g., SEQ ID NO:2). More particularly, the kalirin-derived peptide comprises a fragment of SEQ ID NO:2 containing the sequence ARHLEVRIQD-FVRRVEQRKLLLDMSVSFHTH (residues 3-33 of SEQ ID NO: 3) and peptides having from about 70%, 80%, 85%, 90%, 95%, 98% or 99% identity to the foregoing sequence (including the sequences as set forth in the Table below (SEQ ID NOs:3-26).

| Name | GI | | 1 | KAARHLEVRIQDFVRRVEQRKLLLDMSVSFHTH | 33 |
|------|-----|-----|-----|-----|-----|
| human | 118093831 | 673 | ............................... | | 705 |
| rat | 47933903 | 599 | ............................... | | 631 |

-continued

| | | | | | |
|---|---|---|---|---|---|
| mouse | 82959198 | 617 | ................................. | 649 | |
| dog | 74002910 | 639 | ................................. | 671 | |
| puffer fish | 47221952 | 665 | ....................H.............. | 697 | |
| human | 45439359 | 648 | ..HQ..D..............I............ | 679 | |
| Chipmpanzee | 114599040 | 895 | ..HQ..D..............I............ | 926 | |
| cow | 76646637 | 57 | ..HQ..D..............I............ | 607 | |
| rat | 109464537 | 648 | ..HQ..D..............I............ | 679 | |
| mouse | 113929148 | 589 | ..HQ..D..............I............ | 620 | |
| R.J. fowl | 118086576 | 622 | ..HQ..D..............I............ | 653 | |
| dog | 74002999 | 598 | ..HQ..D..............I.........S. | 629 | |
| zebra fish | 94733856 | 599 | ..HQ..D..............V......A.... | 630 | |
| Zebra fish | 68362538 | 646 | ..H.....V.E..............I....... | 677 | |
| puffer fish | 47224100 | 639 | ..HQ..D..............V......A.... | 670 | |
| puffer fish | 47229500 | 640 | ..HQ..D..............V......A.Q.. | 671 | |
| puffer fish | 47214428 | 481 | ...D.D..S.A.IQ..........LA...Y.. | 518 | |
| Sea Urchin | 115739539 | 38 | ..A..AKVG..IS..A..RQ..V...A..Q. | 68 | |
| Fruit fly | 6708476 | 644 | ..E..LQVGS.AE.....RRR...A.I.Y.. | 674 | |
| fungi | 83767646 | 194 | ......LR.R..QN..G. | 211 | |
| fungi | 50257320 | 140 | .KM.........FN. | 154 | |
| plant | 92889507 | 200 | ....V...... | 210 | |
| bacteria | 83999851 | 424 | ..E.I..Q.... | re435 | |
| Query | | 1 | KAARHLEVRIQDFVRRVEQRKLLLDMSVSFHTH | 33 | |

An NO inhibiting activity of kalirin can be localized to an approximate 33 amino acid segment of kalirin. An active fragment of Kalirin has about 25 amino acids to about 80 amino acids, but can include the full-length of Kalirin (e.g., SEQ ID NO:2). Typically, an active fragment of kalirin has about 28 amino acids to about 37 amino acids and, more commonly, about 30 amino acids to about 35 amino acids. A 33-mer peptide corresponding to amino acids 617 to 649 of kalirin (SEQ ID NO:2) inhibits NO production and/or iNOS activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a one embodiment, the length of a reference sequence aligned for comparison purposes is at least 30%, at least 40%, at least 50%, at least 60%, but typically at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a one embodiment, the percent identity between two amino acid sequences is determined using the GAP program in the GCG software package (available at http:~~www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http:~~www.gcg.com), using a NWSgapdna.CMP matrix and a gap weight of 40, 50, 60, 70, or 80 and a length weight of 1, 2, 3, 4, 5, or 6.

The nucleic acid and protein sequences of the disclosure can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10.

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment of kalirin that retains its activity in alleviating senile dementia or other iNOS or NO associated disorders. An amino acid also can be an amino acid mimetic, which is a structure that exhibits substantially the same spatial arrangement of functional groups as an amino acid but does not necessarily have both the alpha-amino and alpha-carboxyl groups characteristic of an amino acid. Other examples of amino acids and amino acids analogs are listed in Gross and Meienhofer, The Peptides: Analysis, Synthesis, Biology, Academic Press, Inc., New York (1983).

A kalirin polypeptide or active fragment thereof can be isolated or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., Molecular Cloning: A Laboratory Manual, 2nd Ed., Vols. 1 to 3, Cold Spring Harbor Laboratory Press, New York (1989).

Alternatively a kalirin polypeptide or active fragment can be chemical synthesized, for example, by the solid phase peptide synthesis method of Merrifield et al., J. Am. Chem. Soc. 85:2149 (1964). Standard solution methods well known in the art also can be used to synthesize a peptide useful in the disclosure (see, for example, Bodanszky, Principles of Peptide Synthesis, Springer-Verlag, Berlin (1984) and Bodanszky, Peptide Chemistry, Springer-Verlag, Berlin (1993)). A newly synthesized peptide can be purified, for example, by high performance liquid chromatography (HPLC), and can be characterized using, for example, mass spectrometry or amino acid sequence analysis.

It is understood that modifications can be made to a kalirin polypeptide or active fragment without destroying its biological function. Thus, a modification of an active fragment of kalirin that does not destroy its ability to alleviate senile dementia is within the definition of a kalirin polypeptide. A modification can include, for example, an addition, deletion, or substitution of amino acid residues (e.g., 1 to 10); a substitution of a compound that mimics amino acid structure or function; and addition of chemical moieties such as amino or acetyl groups. The activity of a modified peptide in alleviating senile dementia can be assayed using an animal model of senile dementia.

A particularly useful modification of a kalirin polypeptide is one that confers, for example, increased stability. For example, incorporation of one or more D-amino acids or substitution or deletion of lysine can increase the stability of an active fragment of kalirin by protecting against peptide degradation. The substitution or deletion of a lysine residue confers increased resistance to trypsin-like proteases, as is well known in the art (Partridge, supra (1991)).

A useful modification also can be one that promotes peptide passage across the blood-brain barrier, such as a modification that increases lipophilicity or decreases hydrogen bonding. For example, a tyrosine residue added to the C-terminus of a kalirin polypeptide can increase hydrophobicity and permeability to the blood-brain barrier (see, for example, Banks et al., Peptides 13:1289-1294 (1992) and Pardridge, supra (1991)). A chimeric peptide-pharmaceutical that has increased biological stability or increased permeability to the blood-brain barrier, for example, also can be useful in the method of the disclosure.

As used herein, the term "a senile dementia alleviating amount" or "effective amount" means the amount of a kalirin polypeptide useful for causing a diminution in senile dementia, whether by alleviating senile dementia or by inhibiting the onset of senile dementia or reducing causative agents of dementia (e.g., elevated NO). An effective amount to be administered systemically on a daily basis depends on the body weight of the subject. Typically, an effective amount to be administered systemically on a daily basis is about 0.1 µg/kg to about 1000 µg/kg. More commonly, an effective amount to be administered systemically on a daily basis is about 10 µg/kg to about 100 µg/kg. An effective amount of a peptide for alleviating or inhibiting the onset of dementia can be determined empirically using methods well known to those in the art.

The disclosure provides methods of alleviating dementia (e.g., AD) by administering an effective amount of a kalirin polypeptide (e.g., an active fragment of kalirin) intravenously, intramuscularly, intradermally, subcutaneously, intracranially, intracerebrospinally, topically, orally, transdermally, transmucosally, or intranasally. A pharmaceutically acceptable carrier of well known type can be administered with a kalirin polypeptide. Such carriers include, for example, phosphate buffered saline (PBS).

In one aspect, the method of administration comprises a fusion polypeptide comprising a transduction domain (e.g., a PTD) and an active fragment of kalirin. PTDs are typically cationic in nature. These cationic protein transduction domains track into lipid raft endosomes carrying with them their linked cargo and release their cargo into the cytoplasm by disruption of the endosomal vesicle. Examples of PTDs include AntHD, TAT, VP22, cationic prion protein domains and functional fragments thereof. The disclosure provides methods and compositions that combine the use of PTDs such as TAT and poly-Arg, with an active fragment of kalirin to promote uptake into a cell either in vitro or in vivo.

In general, the transduction domain of the fusion molecule can be nearly any synthetic or naturally-occurring amino acid sequence that can transduce or assist in the transduction of the fusion molecule. For example, transduction can be achieved in accord with the disclosure by use of a protein sequence such as an HIV TAT protein or fragment thereof that is covalently linked at the N-terminal or C-terminal end to an active fragment of kalirin. Alternatively, the transducing protein can be the Antennapedia homeodomain or the HSV VP22 sequence, the N-terminal fragment of a prion protein or suitable transducing fragments thereof such as those known in the art.

The type and size of the PTD will be guided by several parameters including the extent of transduction desired. PTDs will be capable of transducing at least about 20%, 25%, 50%, 75%, 80% or 90% of the cells of interest, more typically at least about 95%, 98% and up to, and including, about 100% of the cells. Transduction efficiency, typically expressed as the percentage of transduced cells, can be determined by several conventional methods.

In one aspect, a PTD useful in the methods and compositions of the disclosure comprise a peptide featuring substantial alpha-helicity. It has been discovered that transduction is optimized when the PTD exhibits significant alpha-helicity. In another embodiment, the PTD comprises a sequence containing basic amino acid residues that are substantially aligned along at least one face of the peptide. A PTD domain of the disclosure may be a naturally occurring peptide or a synthetic peptide.

In yet another embodiment, the PTD domain comprises a peptide represented by the following general formula: B1—$X_1$—$X_2$—$X_3$—$B_2$—$X_4$—$X_5$—$B_3$ (SEQ ID NO:27) wherein $B_1$, $B_2$, and $B_3$ are each independently a basic amino acid, the same or different; and $X_1$, $X_2$, $X_3$, $X_4$ and $X_5$ are each independently an alpha-helix enhancing amino acid the same or different. In another embodiment, the PTD domain is represented by the following general formula: B1—$X_1$—$X_2$—$B_2$—$B_3$—$X_3$—$X_4$—$B_4$ (SEQ ID NO:28) wherein $B_1$, $B_2$, $B_3$, and $B_4$ are each independently a basic amino acid, the same or different; and $X_1$, $X_2$, $X_3$, and $X_4$ are each independently an alpha-helix enhancing amino acid the same or different.

Additionally PTD domains comprise basic residues, e.g., lysine (Lys) or arginine (Arg), and further including at least one proline (Pro) residue sufficient to introduce "kinks" into the domain. Examples of such domains include the transduction domains of prions. For example, such a peptide comprises KKRPKPG (SEQ ID NO:29).

In another embodiment the PTD is cationic and consists of between 7 and 10 amino acids and has the formula $KX_1RX_2X_1$ (SEQ ID NO:30) wherein $X_1$ is R or K and $X_2$ is any amino acid. An example of such a peptide comprises RKKRRQRRR (SEQ ID NO:31).

Additional transducing domains in accord with this invention include a TAT fragment that comprises at least amino acids 49 to 56 of TAT up to about the full-length TAT sequence. A TAT fragment may include one or more amino acid changes sufficient to increase the alpha-helicity of the fragment. In some instances, the amino acid changes introduced will involve adding a recognized alpha-helix enhancing amino acid. Alternatively, the amino acid changes will involve removing one or more amino acids from the TAT fragment the impede alpha helix formation or stability. In a more specific embodiment, the TAT fragment will include at least one amino acid substitution with an alpha-helix enhancing amino acid. Typically the TAT fragment will be made by standard peptide synthesis techniques although recombinant DNA approaches may be used in some cases.

Additional transduction proteins (PTDs) that can be used in the compositions and methods of the disclosure include the TAT fragment in which the TAT 49-56 sequence has been modified so that at least two basic amino acids in the sequence are substantially aligned along at least one face of the TAT fragment. Illustrative TAT fragments include at least one specified amino acid substitution in at least amino acids 49-56 of TAT which substitution aligns the basic amino acid residues of the 49-56 sequence along at least one face of the segment and typically the TAT 49-56 sequence.

Also included are chimeric PTD domains. Such chimeric transducing proteins include parts of at least two different transducing proteins. For example, chimeric transducing proteins can be formed by fusing two different TAT fragments, e.g., one from HIV-1 and the other from HIV-2 or one from a prion protein and one from HIV.

PTDs can be linked or fused with an active fragment of kalirin. It will be understood that the PTD may be fused to an active fragment of kalirin or the coding sequences for a PTD and the coding sequence for an active fragment of kalirin may be operably linked such that upon expression in a suitable recombinant cell a fusion polypeptide is provided.

As noted, components of the fusion polypeptides disclosed herein, e.g., a PTD and an active fragment of kalirin, can be organized in nearly any fashion provided that the fusion polypeptide has the function for which it was intended. The fusion polypeptides or chimeric proteins comprising one or more PTDs linked to an active fragment of kalirin may be linked by a peptide linker. Each of the several domains may be directly linked or may be separated by a linker peptide. The domains may be presented in any order Additionally, the fusion polypeptides may include tags, e.g., to facilitate identification and/or purification of the fusion polypeptide, such as a 6xHIS tag (SEQ ID NO: 52).

Peptide linkers that can be used in the fusion polypeptides will typically comprise up to about 20 or 30 amino acids, commonly up to about 10 or 15 amino acids, and still more often from about 1 to 5 amino acids. The linker sequence is generally flexible so as not to hold the fusion molecule in a single rigid conformation. The linker sequence can be used, e.g., to space the PTD domain from an active fragment of kalirin. For example, the peptide linker sequence can be positioned between the protein transduction domain and the kalirin peptide, e.g., to provide molecular flexibility. The length of the linker moiety is chosen to optimize the biological activity of the polypeptide comprising a PTD domain fusion construct and can be determined empirically without undue experimentation. Examples of linker moieties are -Gly-Gly-, GGGGS (SEQ ID NO:32), $(GGGGS)_N$ (SEQ ID NO:33), GKSSGSGSESKS (SEQ ID NO:34), GSTSGSGKSSEGKG (SEQ ID NO:35), GSTSGSGKSSEGSGSTKG (SEQ ID NO:36), GSTSGSGKPGSGEGSTKG (SEQ ID NO:37), or EGKSSGSGSESKEF (SEQ ID NO:38). Linking moieties are described, for example, in Huston et al., Proc. Nat'l Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference.

An isolated polynucleotide of the disclosure include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The polynucleotides of the disclosure include full-length genes or cDNA molecules as well as a combination of fragments thereof. The polynucleotides of the disclosure are typically derived from human sources, but the disclosure includes those derived from non-human species, as well. In one aspect, a polynucleotide of the disclosure comprises (i) a polynucleotide comprising SEQ ID NO:1; (ii) a polynucleotide encoding a polypeptide comprising SEQ ID NO:2; (iii) a polynucleotide encoding an active fragment of SEQ ID NO:2; (iv) a polynucleotide encoding SEQ ID NO:3-25 or 26; (v) a polynucleotide of any one of (i-iv) wherein T can be U; (vi) a complement of any of (i-v); and a polynucleotide that hybridizes to any of (i-vi) under highly stringent conditions and encodes a kalirin polypeptide or active fragment thereof.

An "isolated polynucleotide" is one that has been separated from adjacent genetic sequences present in the genome of the organism from which the polynucleotide was isolated, in the case of polynucleotides isolated from naturally-occurring sources. In the case of polynucleotides synthesized enzymatically from a template or chemically, such as PCR products, cDNA molecules, or oligonucleotides for example, it is understood that the polynucleotides resulting from such processes are isolated polynucleotides. An isolated polynucleotide refers to a polynucleotide in the form of a separate fragment or as a component of a larger polynucleotide construct. In one embodiment, isolated polynucleotides are substantially free from contaminating endogenous material. The polynucleotide typically is derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd sed., Cold Spring Harbor Laboratory, Cold Spring Harbor, N.Y. (1989)). Such sequences are provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The disclosure also includes polynucleotides that hybridize under moderately stringent conditions, and more typically under highly stringent conditions, to the complement of polynucleotides that encode the Kalirin polypeptides or active fragment described herein (e.g., SEQ ID NO:2 or 3, respectively). The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3 6.4), and can be readily determined by those having ordinary skill in the art based on, for example, the length and/or base composition of the DNA. One way of achieving moderately stringent conditions for filter-bound target DNA involves the use of a prewashing solution containing 5×SSC, 0.5% SDS, 1.0 mM EDTA (pH 8.0), hybridization buffer of about 6×SSC, and a hybridization temperature of about 68° C. (or other similar hybridization solutions, such as one containing about 50% formamide, with a hybridization temperature of about 42° C.), and washing conditions of about 60° C., in 0.5×SSC, 0.1% SDS. "SSC" (1×) is 0.15 M NaCl, 0.015 M Na citrate, pH 7.0. Generally, highly stringent conditions are defined as hybridization conditions as above, but with washing at approximately 68° C., 0.2×SSC, 0.1% SDS. If desired, SSPE (1×SSPE is 0.15M NaCl, 10 mM NaH2PO4, and 1.25 mM EDTA, pH 7.4) can be substituted for SSC in the hybridization and wash buffers, and the SDS can be omitted from any of the above buffers without affecting the stringency. Washes are performed for 15 minutes after hybridization is complete. Wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). The hybridization temperature for hybrid duplexes anticipated to be less than 50 base pairs in length optimally is 5 to 10° C. below the melting temperature (Tm) of the duplex, where Tm is determined according to the following equations. For hybrids less than 18 base pairs in length, Tm (° C.)=2(# of A+T bases)+4(# of #G+C bases). For hybrids above 18 base pairs in length, Tm (° C.)=81.5+16.6(log 10 [Na+])+0.41(% G+C)−(600/N), where N is the number of bases in the hybrid, and [Na+] is the concentration of sodium ions in the hybridization buffer ([Na+] for 1×SSC=0.165M). Typically, each such hybridizing polynucleotide has a length that is at least 15 nucleotides (or more typically at least 18 nucleotides, or at least 20 nucleotides, or at least 25 nucleotides, or at least 30 nucleotides, or at least 40 nucleotides, or most commonly at least 50 nucleotides), or at least 25% (at least 50%, or at least 60%, or at least 70%, and most commonly at least 80%) of the length of the polynucleotide of the disclosure to which it hybridizes, and has at least 60% sequence identity (at least 70%, at least 75%, at least 80%, at least 85%, at least 90%, at least 95%, at least 97.5%, or at least 99%, and most preferably at least 99.5%) with the polynucleotide of the disclosure to which it hybridizes, where sequence identity is determined by comparing the sequences of the hybridizing polynucleotides when aligned so as to maximize overlap and identity while minimizing sequence gaps.

The disclosure also provides genes corresponding to the polynucleotide sequences disclosed herein. "Corresponding genes" or "corresponding genomic polynucleotides" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein, for example, for designing probes or PCR primers. Such methods include the preparation of probes or primers from the disclosed sequence information for identification and/or amplification of genes in appropriate genomic libraries or other sources of genomic materials. An "isolated gene" or "an isolated genomic polynucleotide" is a genomic polynucleotide that has been separated from the adjacent genomic sequences present in the genome of the organism from which the genomic polynucleotide was isolated.

The isolated polynucleotide of the disclosure may be operably linked to an expression control sequence such as that in the pDC412 or pDC314 vectors, or the pMT2 or pED expression vectors disclosed in Kaufman et al., Polynucleotides Res. 19, 4485 4490 (1991); and Pouwels et al. Cloning Vectors: A Laboratory Manual, Elsevier, N.Y., (1985), in order to produce the polypeptide recombinantly. Many suitable expression control sequences are known in the art. General methods of expressing recombinant polypeptides are also known, such as those described in R. Kaufman, Methods in Enzymology 185, 537 566 (1990). As used herein "operably linked" means that the polynucleotide of the disclosure and an expression control sequence are situated within a construct, vector, or cell in such a way that the polypeptide encoded by the polynucleotide is expressed when appropriate molecules (such as polymerases) are present. As one embodiment of the disclosure, at least one expression control sequence is operably linked to the polynucleotide of the disclosure in a recombinant host cell or progeny thereof, the polynucleotide and/or expression control sequence having been introduced into the host cell by transformation or transfection, for example, or by any other suitable method.

As another embodiment of the disclosure, at least one expression control sequence is integrated into the genome of a recombinant host cell such that it is operably linked to a polynucleotide sequence encoding a polypeptide of the disclosure. In a further embodiment of the disclosure, at least one expression control sequence is operably linked to a polynucleotide of the disclosure through the action of a trans-acting factor such as a transcription factor, either in vitro or in a recombinant host cell.

In addition, a sequence encoding a signal peptide (native or heterologous) that promotes secretion can be incorporated into expression vectors. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. A DNA sequence for a signal peptide (secretory leader) can be fused in frame to the polynucleotide sequence of the disclosure so that the DNA is initially transcribed, and the mRNA translated, into a fusion polypeptide comprising the signal peptide. A signal peptide that is functional in the intended host cells is one that promotes extracellular secretion of the polypeptide in that host cell. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, R. J., Large Scale Mammalian Cell Culture, 1990, pp. 15 69). Additional protocols using commercially available reagents, such as Lipofectamine lipid reagent (Gibco/BRL) or Lipofectamine-Plus lipid reagent, can be used to transfect cells (Felgner et al., Proc. Natl. Acad. Sci. USA 84:7413 7417, 1987). In addition, electroporation can be used to transfect mammalian cells using conventional procedures, such as those in Sambrook et al. (Molecular Cloning: A Laboratory Manual, 2 ed. Vol. 1 3, Cold Spring Harbor Laboratory Press, 1989). Selection of stable transformants can be performed using methods known in the art, such as, for example, resistance to cytotoxic drugs. Kaufman et al., Meth. in Enzymology 185:487 511, 1990, describes several selection schemes, such as dihydrofolate reductase (DHFR) resistance. A suitable strain for DHFR selection is CHO strain DX-B11, which is deficient in DHFR (Urlaub and Chasin, Proc. Natl. Acad. Sci. USA 77:4216 4220, 1980). A plasmid expressing the DHFR cDNA can be introduced into strain DX-B11, and only cells that contain the plasmid can grow in the appropriate selective medium. Other examples of selectable markers that can be incorporated into an expression vector include cDNAs conferring resistance to antibiotics, such as G418 and hygromycin B. Cells harboring the vector can be selected on the basis of resistance to these compounds.

A number of types of cells may act as suitable host cells for expression of a kalirin polypeptide or active fragment thereof. Mammalian host cells include, for example, the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) as described by McMahan et al. (EMBO J. 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, the polypeptide may be produced in lower eukaryotes such as yeast or in prokaryotes such as bacteria. Suitable yeast strains include *Saccharomyces cerevisiae, Schizosaccharomyces pombe, Kluyveromyces* strains, *Candida* spp., *Pichia* spp. or any yeast strain capable of expressing heterologous polypeptides. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain a functional Kalirin polypeptide. Such covalent attachments may be accomplished using known chemical or enzymatic methods. The polypeptide may also be produced by operably linking the isolated polynucleotide of the disclosure to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, Bio/Technology 6:47 (1988). As used herein, an insect cell that is modified to express an exogenous polynucleotide of the disclosure is considered "transformed." Cell-free translation systems may also be employed to produce polypeptides using RNAs derived from polynucleotide constructs disclosed herein. A host cell that comprises an isolated polynucleotide of the disclosure, preferably operably linked to at least one expression control sequence, is a "recombinant host cell".

The polypeptide of the disclosure may be prepared by culturing transformed host cells under culture conditions suitable to support expression of the recombinant polypeptide. The resulting expressed polypeptide may then be purified from such culture (i.e., from culture medium or cell extracts) using known purification processes, such as selective precipitation with various salts, gel filtration and ion exchange chromatography. The purification of the polypeptide may also include an affinity column containing agents that will bind to the polypeptide; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography using an antibody that specifically binds one or more Kalirin epitopes.

Alternatively, the polypeptide of the disclosure may also be expressed in a form that will facilitate purification. For example, it may be expressed as a fusion polypeptide, that is, it may be fused with a maltose binding polypeptide (MBP), glutathione-5-transferase (GST), thioredoxin (TRX) or poly-HIS. Kits for expression and purification of such fusion polypeptides are commercially available from New England BioLab (Beverly, Mass.), Pharmacia (Piscataway, N.J.) and InVitrogen, respectively. The polypeptide can also be tagged with a non-Kalirin epitope and subsequently purified by using a specific antibody directed to such epitope. One such epitope (FLAG®) is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. The polypeptide thus purified is substantially free of other mammalian polypeptides and is defined in accordance with the disclosure as an "isolated polypeptide." The described purification method may be used to isolate Kalirin and Kalirin fragments as well as antibodies that bind to Kalirin polypeptides, fragments, variants, binding partners etc. The polypeptide of the disclosure may also be expressed as a product of transgenic animals, e.g., as a component of the milk of transgenic cows, goats, pigs, or sheep which are characterized by containing somatic or germ cells into which has been inserted a polynucleotide encoding a human Kalirin polypeptide.

It is also possible to utilize an affinity column comprising a polypeptide capable of binding to Kalirin polypeptides, such as a monoclonal antibody generated against Kalirin or against an antigenic fragment thereof, to affinity-purify expressed Kalirin polypeptides. These Kalirin polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure. In this aspect of the disclosure, Kalirin-binding polypeptides, such as the anti-Kalirin antibodies of the disclosure or other polypeptides that can interact with Kalirin or fragments thereof, can be bound to a solid phase support such as a column chromatography matrix or a similar substrate suitable for identifying, separating, or purifying cells that express polypeptides of the disclosure on their surface. Adherence of Kalirin-binding polypeptides of the disclosure to a solid phase contacting surface can be accomplished by any means, for example, magnetic microspheres can be coated with these polypeptide-binding polypeptides and held in the incubation vessel through a magnetic field. Suspensions of cell mixtures are contacted with the solid phase that has such polypeptide-binding polypeptides thereon. Cells having polypeptides of the disclosure on their surface bind to the fixed Kalirin-binding polypeptide and unbound cells then are washed away. This affinity-binding method is useful for purifying, screening, or separating such Kalirin-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing polypeptide-expressing cells of the disclosure first can be incubated with a biotinylated Kalirin-binding polypeptide of the disclosure. The resulting mixture then is passed through a column packed with avidin-coated beads, whereby the high affinity of biotin for avidin provides the binding of the polypeptide-binding cells to the beads. Use of avidin-coated beads is known in the art. See Berenson, et al. J. Cell. Biochem., 10D:239 (1986). Wash of unbound material and the release of the bound cells is performed using conventional methods.

The polynucleotides encoding the Kalirin polypeptides provided by the disclosure can be used for numerous diagnostic or other useful purposes. The polynucleotides of the disclosure can be used to express recombinant Kalirin polypeptide for analysis, characterization or therapeutic use; as markers for tissues in which the corresponding polypeptide is preferentially expressed (either constitutively or at a particular stage of tissue differentiation or development or in disease states); as molecular weight markers on Southern gels; as chromosome markers or tags (when labeled); to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-polypeptide antibodies using DNA immunization techniques; as an antigen to raise anti-DNA antibodies or elicit another immune response, and for use in gene therapy.

Uses of Kalirin polypeptides and fragmented polypeptides include, but are not limited to, the following: purifying polypeptides and measuring the activity thereof; delivery agents; therapeutic and research reagents; molecular weight and isoelectric focusing markers; controls for peptide fragmentation; identification of unknown polypeptides; and preparation of Kalirin-specific antibodies. Any or all polynucleotides suitable for these uses are capable of being developed into reagent grade materials or kit format for commercialization as products. Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Among the uses of the disclosed Kalirin polynucleotides, and combinations of fragments thereof, is the use of fragments as probes or primers. Such fragments generally comprise at least about 17 contiguous nucleotides of a DNA sequence. In other embodiments, a DNA fragment comprises at least 30, or at least 60, contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human Kalirin homologues.

The polynucleotides encoding Kalirin polypeptides, and the disclosed fragments and combinations of these polynucleotides, can be used by those skilled in the art as a chromosome marker. In addition, polynucleotides of the disclosure or a fragment thereof can be used as a positional marker to map other genes of unknown location. Useful techniques include, but are not limited to, using the Kalirin polynucleotide sequence or portions thereof, including oligonucleotides, as a probe in various well-known techniques such as radiation hybrid mapping (high resolution), in situ hybridization to chromosome spreads (moderate resolution), and Southern blot hybridization to hybrid cell lines containing individual human chromosomes (low resolution).

The polynucleotides encoding Kalirin polypeptides, and the disclosed fragments and combinations of these polynucleotides can be used by one skilled in the art using well-known techniques to analyze abnormalities associated with the Kalirin gene or variants thereof. By this means, one can distinguish conditions in which this marker is rearranged or deleted and can use this information for diagnosing certain medical disorders. Kalirin DNA furthermore can be used in developing treatments for any disorder mediated (directly or indirectly) by defective, or insufficient amounts of, the genes corresponding to the polynucleotides of the disclosure. Disclosure herein of native nucleotide sequences permits the detection of defective genes, and the replacement thereof with a normal Kalirin gene using gene therapy techniques known in the art. Defective genes can be detected in in vitro diagnostic assays, and by comparison of a native nucleotide sequence disclosed herein with that of a gene derived from a person suspected of harboring a defect in a Kalirin gene.

In one aspect the disclosure relates to a method to identify modulators useful to treat, prevent or ameliorate pathological conditions associated with excess iNOS activity or NO, including, but not limited to Alzheimer's Disease comprising: a) assaying for the ability of a candidate agent to modulate kalirin activity or production and which can further include b) assaying for the ability of an identified agent to reverse the pathological effects observed in animal models of said conditions and/or in clinical studies with subjects with any one or more of said conditions.

Conventional screening assays (both in vitro and in vivo) may be used to identify agents the modulate kalirin protein activity and/or gene expression. Protein activity levels, e.g., enzymatic activity levels, can be assayed in a subject using a biological sample from the subject using conventional enzyme activity assays (e.g., to determine iNOS activity of NO in a sample). Gene expression (e.g., mRNA levels) may also be determined using methods familiar to one of skill in the art, including, for example, conventional Northern analysis or commercially available microarrays. Additionally, the effect of test agent on protein levels can be detected with an ELISA antibody-based assay or fluorescent labelling reaction assay. These techniques are readily available for high throughput screening and are familiar to one skilled in the art.

Data gathered from these studies would be used to identify kalirin agonists with therapeutic usefulness for the treatment of pathological conditions discussed herein. Such agonists could be further assayed in conventional live animal models familiar to one of skill in the art and/or in clinical trials with humans according to conventional methods to assess the ability of said agent/agonist to treat, prevent or ameliorate any one or more of said conditions in vivo.

In another aspect, the disclosure relates to a method to treat, prevent or ameliorate pathological conditions associated with iNOS activity and NO including, but not limited to, Alzheimer's Disease, comprising administering to a subject in need thereof a pharmaceutical composition comprising an effective amount of a kalirin agonist.

The pharmaceutical compositions can comprise substances that inhibit the expression of other agents associated with the modulation of NO including, iNOS and homologs thereof. Such molecules include ribozymes, antisense oligonucleotides, triple helix DNA, RNA aptamers, siRNA and/or double or single stranded RNA directed to an appropriate nucleotide sequence of nucleic acid encoding, for example, iNOS. These inhibitory molecules may be created using conventional techniques by one of skill in the art without undue burden or experimentation. For example, changes in polynucleotide expression in a cell can be obtained by designing vectors capable of expression of a desired molecule (e.g., a kalirin 7 polynucleotide, antisense iNOS and the like) by operably liking the desired molecule to control regions, i.e. to promoters, enhancers, and introns.

Vectors may be introduced into cells or tissues by many available means, and may be used in vivo, in vitro or ex vivo. For ex vivo therapy, vectors may be introduced into stem cells taken from the patient and clonally propagated for autologous transplant back into that same patient. Delivery by transfection and by liposome injections may be achieved using methods that are well known in the art.

The disclosure also provide methods and compositions for determining diagnosing or determining the risk of a subject for developing senile dementia (e.g., AD). The method comprises monitoring levels of kalirin polypeptides or activity and/or detecting gene expression (mRNA levels) in a subject.

Suitable antibodies for use in diagnostic methods and kits described herein may be obtained from a commercial source or produced according to conventional methods based upon the polypeptide sequence provided herein. Such antibodies may include, but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

For the production of antibodies to the polypeptides discussed herein, various host animals may be immunized by injection with the polypeptides, or a portion thereof. Such host animals may include, but are not limited to, rabbits, mice, goats, chicken, and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Detection method for use with antibodies are known in the art. For example, antibody detection may be achieved using standard ELISA, FACS analysis, and standard imaging techniques used in vitro or in vivo. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials.

In another aspect, the disclosure provides methods of treating neurodegenerative disorder and/or senile dementia comprising (i) stimulating production of kalirin in vivo and (ii) by gene therapy techniques. Kalirin gene products or therapeutic treatments can be obtained via homologous recombination, or "gene targeting," techniques. Such techniques employ the introduction of exogenous transcription control elements (such as the CMV promoter or the like) in a particular predetermined site on the genome, to induce expression of the endogenous polynucleotide sequence of interest (see, for example, U.S. Pat. No. 5,272,071). The location of integration into a host chromosome or genome can be easily determined by one of skill in the art, given the known location and sequence of the gene. In one embodiment, the disclosure contemplates the introduction of exogenous transcriptional control elements in conjunction with an amplifiable gene, to produce increased amounts of the gene product, again, without the need for isolation of the gene sequence itself from the host cell.

Because mutant or reduced kalirin polypeptide correlates with the excessive accumulation nitric oxide, the regulation of kalirin expression finds use in gene therapy to treat neurodegeneratie diseases associated with excess iNOS activity or NO production. In particular, to reduce the activity of iNOS or nitric oxide production, a functional kalirin gene or a polynucleotide encoding an active fragment of kalirin may be introduced into cells at the sites of excess iNOS activity or NO production such that the cell expresses a therapeutically effective amount of kalirin polypeptide or active fragment thereof.

Adenoviral, adeno-associated, herpes virus, vaccinia, retroviral, or other viral vectors with the appropriate tropism for cells likely to be involved in neurodegenerative diseases such as AD may be used as a gene transfer delivery system for a therapeutic kalirin genetic construct. Viral vectors which do not require that the target cell be actively dividing, such as adenoviral and adeno-associated vectors, are particularly useful when the cells are accumulating but not particularly proliferative. Numerous vectors useful for this purpose are generally known (Miller, Human Gene Therapy 15-14, 1990; Friedman, Science 244:1275-1281, 1989; Eglitis and Anderson, BioTechniques 6:608-614, 1988; Tolstoshev and Anderson, Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; and Miller and Rosman, Biotechniques 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

By inserting a kalirin polynucleotide or oligonucleotide of interest into the viral vector, along with another gene which encodes the ligand for a receptor on a specific target cell, for example, the vector is now target specific. Viral vectors can be made target specific by attaching, for example, a sugar, a glycolipid, or a protein. Preferred targeting is accomplished by using an antibody to target the viral vector. Those of skill in the art will know of, or can readily ascertain without undue experimentation, specific polynucleotide sequences which can be inserted into the viral genome or attached to a viral envelope to allow target specific delivery of the viral vector containing a kalirin polynucleotide or oligonucleotide, e.g., the human wild-type kalirin polynucleotide.

Since recombinant viruses are defective, they require assistance in order to produce infectious vector particles. This assistance can be provided, for example, by using helper cell lines that contain plasmids encoding all of the structural genes of the virus under the control of regulatory sequences within the viral genome. These plasmids are missing a nucleotide sequence which enables the packaging mechanism to recognize a polynucleotide transcript for encapsidation. These cell lines produce empty virions, since no genome is packaged. If a viral vector is introduced into such cells in which the packaging signal is intact, but the structural genes are replaced by other genes of interest, the vector can be packaged and vector virion produced.

Non-viral approaches may also be employed for the introduction of therapeutic kalirin polynucleotide or oligonucleotide into cells otherwise predicted to have excessive iNOS activity or NO accumulation. For example, kalirin or an active fragment thereof may be introduced by the techniques of colloidal dispersion (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

Colloidal dispersion systems include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macro molecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipid, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

For any of the above approaches, the therapeutic kalirin polynucleotide or oligonucleotide construct is applied to the site where iNOS activity is to be controlled or NO production reduced (for example, by injection), but may also be applied to tissue in the vicinity of the iNOS or NO production or even to a blood vessel supplying the cells where control of iNOS activity or NO production is desired.

In the gene therapy constructs, kalirin polynucleotide or oligonucleotide expression is directed from any suitable promoter (e.g., the human cytomegalovirus, simian virus 40, actin or adenovirus constituative promoters; or the cytokine or metallothionein promoters for activated synoviocyte specific expression). Furthermore, kalirin production may be regulated by any desired mammalian regulatory element. For example, if desired, enhancers known to direct preferential gene expression can be used to direct kalirin expression. Such enhancers include, without limitation, those enhancers which are characterized as tissue or cell specific in their expression.

Alternatively, if a kalirin genomic clone is utilized as a therapeutic construct, kalirin expression is regulated by its cognate regulatory sequences or, if desired, by regulatory sequences derived from a heterologous source, e.g., any of the promoters or regulatory elements described above.

Less preferably, kalirin gene therapy is accomplished by direct administration of a kalirin mRNA to a cell predicted to require iNOS or NO control. This mRNA may be produced and isolated by any standard technique, but is most readily produced by in vitro transcription using a cDNA encoding a kalirin or active fragment under the control of a high efficiency promoter (e.g., the T7 promoter). Administration of kalirin mRNA to accumulated cells is carried out by any of the methods for direct nucleic acid administration described above.

Ideally, the production of a kalirin or active fragment by any gene therapy approach described above results in a cellular level of the polypeptide that is at least equivalent to the normal, cellular level of kalirin in an unaffected individual. Treatment by any kalirin-mediated gene therapy approach may be combined with more traditional therapies.

In yet another aspect, the upstream regulatory region of kalirin may be modified to induce expression of a kalirin polypeptide. In humans kalirin-7 is located 3q21.1-q21.2 on chromosome 3. FIG. 8 provides the upstream regulatory sequence of kalirin 7. In one aspect, the regulatory sequence may be targeted with a heterologous regulatory domain that provides controlled or constitutive expression of kalirin 7 in subjects that have excessive or reduced expression of kalirin 7. For example, where a tissue has excessive iNOS activity or increased NO content, a heterologous regulatory domain may be targeted upstream of kalirin (using the gene therapy techniques described above), such that the downstream kalirin polynucleotide is regulated by the heterologous regulatory domain.

The following examples are intended to illustrate but not limit the disclosure.

EXAMPLE

AD patients and brain specimens—Brain specimens (1.6 cm×0.6 cm×0.5 cm) were obtained from the University of Kentucky Alzheimer's Disease Research Center. All AD patients met standard clinical and neuropathological criteria for the diagnosis of AD. Age- and sex matched control subjects (Table III) were followed longitudinally and showed no evidence of cognitive decline and only age-related brain alterations at autopsy. Hippocampal and cerebellar samples were removed at autopsy, immediately immersed in liquid $N_2$ and stored at $-70°$ C. The study used 19 AD and 15 control hippocampi and cerebella. The postmortem interval ranged from 2 to 4 h with a mean of 2.9±0.9. The weights of AD brains were not significantly different from the controls. Since ApoE isoforms, ApoE2 ($Cys^{112}/Cys^{158}$), ApoE3 ($Cys^{112}/Arg^{158}$) and ApoE4 ($Arg^{112}/Arg^{158}$), correlate with late onset AD, they were genotyped. The majority (84%) of the AD patients carried one or both ApoE4 alleles, whereas the majority (67%) of the controls were ApoE3/ApoE3 and 27% of the controls carried only one ApoE4 copy. Thus, ApoE typing shows that the samples reflect the general AD and control populations.

RNA extraction—Frozen samples from the hippocampus and cerebellum were thawed, weighed, and placed in 10 volumes of Trizol (Invitrogen). They were then homogenized in a micro-homogenizer for three-six 20 s bursts at the maximum speed, which was repeated 3-6 times. Total RNA was extracted from the homogenized tissues and also from transfected cells in Trizol according to the manufacture's instructions (Invitrogen). The RNA concentration was determined by absorption at 260 nm.

Gene expression analysis—Biotinylated cDNA was synthesized from 10 μg of total RNA, and hybridized to the U133A GeneChip (Affymetrix) at 45° C. for 16 h. The chips were washed, stained, and scanned using an Affymetrix GeneChip scanner. Labeling, hybridization and scanning were carried out according to the manufacturer's protocol. Raw image data were processed and normalized using Microarray Analysis suite 5.0. Data analysis was performed by SAS program version 8.2 and statistical analysis was performed by two-way ANOVA test to determine the p values (significance) of the differences between AD and control values. In addition to the p values, standard deviations among duplicates in repeats of a sample were also calculated.

Quantitative RT-PCR—First strand cDNAs were synthesized from 2 μg of total RNA extract using oligo(dT) and Superscript II reverse transcriptase (Invitrogen). They were amplified by PCR with platinum Taq DNA polymerase (Invitrogen) in 1.5 mM $MgCl_2$ in the manufacturer's buffer. The PCR regimen consisted of initial denaturation at 94° C. for 2 min, followed by 23-27 cycles 94° C. for 30 s, 58° C.-62° C. for 30 s and 72° C. for 1 min. PCR products were separated on 1.5% agarose gels. PCR was performed at least three times for each sample. GAPDH (accession number M33197) was used as an internal standard and normalization. The PCR products were analyzed on a Typhoon 8600 scanner (Amersham). The following primers were used for PCR; human Kalirin forward primer (5'-CATGCGGGCACCTTCTTTG-3' (SEQ ID NO:39)), human Kalirin reverse primer (5'-GTTTTAT-TGTCTGAGGATGGGG-3' (SEQ ID NO:40)) (in the DH-PH boundary in GEFL), human iNOS forward primer (5'-CTTCAGTATCACAACCTCAGC-3' (SEQ ID NO:41)), human iNOS reverse primer (5'-GATGTGTTCAAA-CATTTCCCGG-3' (SEQ ID NO:42)), GAPDH forward primer (5'-CAACGGATTTGGTCGTATTGG-3' (SEQ ID NO:43)), and GAPDH reverse primer (5'-CAGTGGACTC-CACGACGTACT-3' (SEQ ID NO:44)).

Real-time PCR—Real-time PCR was performed using a BioRad iQ iCycler Detection System (BioRad Laboratories, Ltd) with SYBR green fluorophore (iQ Super-mix, BioRad). Reactions were performed in a total volume of 25 μl including 12.5 μl 2× SYBR Green iQ Super Mix (BioRad), 1 μl of each primer at 10 μM concentration, and 1 μl of the previously reverse-transcribed cDNA template. Thermal cycling conditions were as follows: an initial incubation at 95° C. for 2 min to activate the polymerase followed by 40 cycles of 95° C. for 30 s, 57° C. for 30 s and 72° C. for 30 s, and a final incubation at 72° C. for 1 min. A melt curve analysis was performed following every run to ensure a single amplified product for every reaction. PCR fluorophore acquisition temperatures were set at 1° C. below the melt curve peak. All reactions were performed in duplicate for every sample. The same reference standard dilution series (single cut Kalirin plasmid DNA) was repeated on every experimental plate and quantifications of both the Kalirin and the GAPDH are based on this using iCycler iQ Optical System Software Version 3.0a (BioRad). Duplicate negative controls (no template cDNA) were also run with every experimental plate to assess specificity and indicate potential contamination. GAPDH was used for relative quantification. The forward and reverse primers were 5'-TGGAGAGTCAATGCTCAACG-3' (SEQ ID NO:45) and 5'-GTCTTCTGCAAGGAAGTGGC-3' (SEQ ID NO:46) for human Kalirin (at the $7^{th}$ spectrin repeat), and 5'-TGCAC-CACCACCAACTGCTTA-3' (SEQ ID NO:47) and 5'-GAG-GCAGGGATGATGTT-3' (SEQ ID NO:48) for human GAPDH. These primers for real-time PCR differ from those used for quantitative RT-PCR, because they were designed by BioRad based on an optimal product length of ~120 bases and optimal sequences for real-time PCR. To test the fidelity of the two different sets of the primers and the PCR methods, the real-time PCR primers were used for quantitative RT-PCR. The results were the same regardless of the primers, verifying the concentrations of mRNAs.

Genomic DNA purification and ApoE typing—Genomic DNA was purified from 25 μg of the brain tissues using QIAamp DNA mini kit (QIAgen) according to the manufacturer's instruction. Twenty five of each genomic DNA sample was amplified using platinum Taq DNA polymerase (Invitrogen) in 1.5 mM $MgCl_2$ in the manufacturer's buffer. The PCR regimen consisted of initial denaturation at 94° C. for 2 min, 35 cycles of 94° C. for 1 min, 58° C. for 1 min and 72° C. for 2 min, and termination at 72° C. for 10 min. The human ApoE forward primer, 5'-CGGAGGAGACGCGGGCAC-3' (SEQ ID NO:49), and ApoE reverse primer, 5'-TCAGTGATTGTCGCTGGGCAC-3' (SEQ ID NO:50), were designed to cover the ApoE2, ApoE3 and ApoE4 polymorphism, based on the ApoE gene sequence. PCR products were resolved on 1.5% agarose gels, extracted and purified with QIAquick gel extraction kit (QIAgen) according to the manufacturer's instruction. Purified DNAs were directly sequenced on CEQ 2000 sequencer (Beckman).

Immunoblot and immunoprecipitation—Proteins were extracted. Brain samples were directly solubilized in 10 volume of lysis buffer (50 mM Tris HCl at pH 7.5, 120 mM NaCl, 5 mM EDTA, 1% Nonidet P-40 (0.3 mg/ml), 8 μg/ml aprotinin, 2 μg/ml pepstatin A, 2 μg/ml leupeptin, 1 mM $Na_3VO_4$, 50 mM NaF and 0.2% of SDS) using Omni 2000 homogenizer (Omni International Inc). The solubilized samples were centrifuged at 15,000×g for 10 min, the supernatants were saved, and protein concentration was measured by the Bradford method. Cultured cells were suspended in another lysis buffer consisting of 100 mM Tris HCl (pH7.5), 150 mM NaCl, 2 mM EDTA, 0.5% of Triton X-100, 1 mM PMSF, 4 μg/ml aprotinin, 1 μg/ml pepstatin A, 1 μg/ml leupeptin, 1 mM $Na_3VO_4$, 50 mM NaF and 0.2% of SDS), and processed.

An equal protein-amount of solubilized supernatants was resolved by SDS-PAGE and blotted onto polyvinylidene difluoride membrane. The membranes were incubated for 1 h in blocking solution containing 3% bovine serum albumin. The membranes were incubated for 1 h with primary antibodies diluted 1:500 in Tris-buffered saline containing 0.1% Tween 20. After washing, membranes were incubated for 1 h in 1:10,000 dilution of secondary antibodies coupled to horseradish peroxidase. Bands were visualized using a chemiluminescent peroxidase substrate (Sigma). Rabbit anti-actin antibodies and mouse anti-Flag M2 antibodies were purchased from Sigma. Blots were scanned, and the band intensity was digitized and quantified using Molecular Dynamics Image Quant 5.1.

The 15,000×g supernatants were sequentially incubated with immunoprecipitation antibody-Sepharose 4B for 4 h at 4° C. (anti-iNOS or anti-Kalirin 7). After washing four times, the Sepharose gels were boiled in SDS and β-mercaptoethanol and the samples were electrophoresed. The gel was immunoblotted.

Radio-iodination—The 15,000×g supernatants were individually mixed with 0.2 mCi of $Na^{125}I$ in 0.1M NaOH and 7 μl of chloramine T (1 mg/ml) in 10 mM $Na_2HPO_4$. After 30 s, 7 μl of sodium metabisulfite (2.5 mg/ml) in 10 mM $Na_2HPO_4$ (pH 7.4) was introduced to terminate radio-iodination. Radio-iodinated proteins were separated from the nonreacted $^{125}I$ on a small Sephadex G-150 column with PBS.

Assays for iNOS and NOS—The hippocampal and cerebellar specimens and the transfected cells were homogenized in 50 mM Tris HCl (pH 7.4), 1 mM EDTA, 0.1 mM tetrahydrobiopterin, 2 mM dithiothreitol, 10% (v/v) glycerol, aprotinin (25 μg/ml), leupeptin (25 μg/ml), 100 μM PMSF, 10 μM FMN, and 10 μM FAD. The homogenates were centrifuged at 2,000×g for 15 min, and the supernatants were assayed for iNOS. iNOS was also assayed in the presence of 10 mM Canavanine (Sigma) or L-NAME (Sigma). The collective activity of NOS (including eNOS, nNOS and iNOS) was determined in an identical fashion to iNOS activity, but in the presence of 1.25 mM $Ca^{2+}$.

Preparation of Aβ1-42 peptide—One mM of A β1-42 (Biosource) was prepared in a capped vial at 37° C. for 5 days, and stored at −20° C. The frozen stock solution was diluted and used at the final concentration of 10 μM.

Cell culture and transfection—AtT-20 cells (ATCC# CCL-89), SH-SY5Y cells (ATCC# CRL-2266), C6 cells (ATCC# CCL-107) and Neuro-2A cells (ATCC # CCL-131) were cultured according to the supplier's instructions. Each cell line was grown in a 25 $cm^2$ flask, stably transfected with pcDNA4 vector carrying Kalirin-7 or pcDNA3 carrying iNOS, using SuperFect transfection reagents (Qiagen) following the manufacture's instructions. Stable cell lines were selected using 0.5 mg/ml of G-418 for pcDNA3 or 0.12 μg/ml of zeocin for pcDNA4.

To induce the iNOS activity, cell lines were transfected with iNOS in pcDNA3 or stimulated with 3 μg/ml of lipopolysaccharides (LPS) for 12-16 h (27) or 10 μM A β1-42 peptide for 18 h. Two different approaches of double transfection with Kalirin-7 and iNOS were used to determine the effects of Kalirin-7 on iNOS. The cell line stably expressing Kalirin-7 was transiently transfected with iNOS, and conversely, the cell line stably expressing iNOS was transiently transfected with increasing amounts of pcDNA4 carrying Kalirin-7 or Kalirin domains.

To test the putative toxic effect of high concentrations of plasmid DNA, up to 2.5 μg, the Renilla luciferase assay (Promega) was used as a transfection reference. The AtT-20 cells stably expressing iNOS were transiently transfected with a constant amount of the pRL-TK vector (Promega) carrying Renilla luciferase and increasing amounts of the Kalirin plasmid. The co-transfected cells were assayed for iNOS and luciferase following the manufacturer's instructions.

In this study, specimens of hippocampi and cerebella were examined from 19 Alzheimer's patients in comparison with 15 control tissues from age- and sex-matched individuals. The genotyping results indicate that the AD patients and control subjects reflect the general AD and control populations.

Over-expressed genes and under-expressed in AD hippocampus—The hippocampus is the most sensitive region of the brain to AD, whereas the cerebellum is the least sensitive region of the brain and therefore used for an internal reference. To identify genes aberrantly expressed in the brain tissue of individuals with AD, RNA extracts from the hippocampus and cerebellum of the AD and control brains were analyzed. To enhance the accuracy of the analyses, individual samples, rather than pooled samples, were analyzed.

Gene expression levels of the individual specimens were determined with the Affymetrix HG-U133A GeneChip. The levels of genes expressed in hippocampal specimens of AD were compared with the expression levels in control hippocampal specimens. The resulting expression ratio of AD/control was compared with the ratios of other genes and those of cerebellar specimens. The results of candidate genes were confirmed with quantitative RT-PCR and real time PCR.

In the analysis, marginally expressed genes had a disproportionately high impact on the differential expression ratios between AD and normal samples. To overcome this problem, these marginally expressed genes were excluded and a statistical significance of $p<0.01$ was used as a criterion for identifying genes with significant expression differences. In addi tion, glyceraldehyde-3-phosphate dehydrogenase (GAPDH) was chosen as the internal reference, since the data demonstrated that its expression was one of the highest and invariant regardless of AD, control, hippocampus and cerebellum. The top 15 over-expressed genes and under-expressed hippocampal genes are listed in Tables I-II; additional data on cerebellar over- and under-expressed genes and on constant genes are in IV-VII.

TABLE I

Top 15 Over-expressed genes in AD hippocampi

| Gene Name | Unigene | p value | AD hippocampus | | Control hippocampus | | AD/C |
|---|---|---|---|---|---|---|---|
| | | | Intensity | Relative intensity | Intensity | Relative intensity | |
| adipocyte enhancer binding protein 1 | Hs.118397 | 4.92E−04 | 951 ± 582 | 0.053 ± 0.035 | 381 ± 113 | 0.029 ± 0.008 | 2.24 |
| Consensus: angiotension receptor-like 1 | Hs.9305 | 3.99E−03 | 2,794 ± 2,145 | 0.173 ± 0.133 | 1,339 ± 556 | 0.101 ± 0.042 | 2.09 |
| annexin A1 (ANXA1) | Hs.78225 | 1.28E−03 | 741 ± 465 | 0.046 ± 0.029 | 375 ± 174 | 0.028 ± 0.013 | 1.97 |
| chemokine receptoe CXCR4 | — | 3.06E−06 | 535 ± 205 | 0.039 ± 0.013 | 325 ± 129 | 0.024 ± 0.010 | 1.95 |
| complement subcomponent C1s, a- and b- | Hs.169756 | 3.67E−04 | 593 ± 469 | 0.055 ± 0.029 | 465 ± 181 | 0.035 ± 0.014 | 1.92 |
| paliadin (KIAA0992) | Hs.194431 | 6.17E−04 | 2,634 ± 1,387 | 0.163 ± 0.086 | 1,419 ± 734 | 0.107 ± 0.055 | 1.86 |
| Consensus: transcriptional co-activator with PDZ | Hs.24341 | 2.85E−05 | 689 ± 257 | 0.043 ± 0.016 | 377 ± 158 | 0.028 ± 0.012 | 1.83 |
| lysosomal memorane glycoprotein-2 | Hs.8262 | 3.19E−03 | 1,335 ± 803 | 0.083 ± 0.050 | 755 ± 348 | 0.057 ± 0.026 | 1.77 |
| insitol 1,4,5-trisphosphate 3-kinase B | Hs.78877 | 1.70E−05 | 3,077 ± 984 | 0.191 ± 0.061 | 1,792 ± 751 | 0.135 ± 0.057 | 1.72 |
| Consensus: KIAA0477 gene product | Hs.129928 | 1.85E−04 | 938 ± 360 | 0.058 ± 0.022 | 551 ± 187 | 0.041 ± 0.014 | 1.70 |
| Consensus: Caxeolin 1(22 kDa) | Hs.74034 | 6.73E−04 | 565 ± 247 | 0.035 ± 0.015 | 346 ± 114 | 0.026 ± 0.009 | 1.63 |
| mannosidase, a. class 2A, member 1 | Hs.32965 | 1.36E−03 | 1,357 ± 604 | 0.084 ± 0.037 | 840 ± 404 | 0.063 ± 0.030 | 1.62 |
| Consensus: dimethylarginine methylamiohydrolase2 | Hs.247362 | 1.46E−03 | 639 ± 245 | 0.040 ± 0.015 | 399 ± 169 | 0.030 ± 0.014 | 1.62 |
| sushi-repeat-Containing protein | Hs.15154 | 2.74E−03 | 563 ± 283 | 0.054 ± 0.018 | 545 ± 148 | 0.041 ± 0.011 | 1.59 |
| H2B histone family, member A | Hs.247817 | 3.04E−04 | 695 ± 262 | 0.043 ± 0.016 | 440 ± 32 | 0.033 ± 0.007 | 1.58 |

The expression intensitites of a gene in AD hippocampaly speciments and control hippocampal specimens were averaged to calculate the means and standard deviations. The ratio of the AD mean/control mean is presented along with the p value of the two sets of intensities. Marginally expressed genes and those with p values ≧ 0.01 were excluded in the analyses for Tables II–V. The relative intesities were calculated by dividing the intensities of a specimen by th entensity of GAPDH (~10,000) of the same specimen, which is one of the highest. The expression intensities of the enzyme were invariant amondg the AD and control specimens with the ratio of 0.96 for the hippocampus and 0.93 for the cerebellum, and the expression level was one of the highest. Because of these reasons, GAPDH serves as a good internal reference for studies on AD.

TABLE II

Top 15 Under-expressed genes in AD hippocampi.

| Gene Name | Unigene | p value | AD hippocampus | | Control hippocampus | | AD/C |
|---|---|---|---|---|---|---|---|
| | | | Intensity | Relative intensity | Intensity | Relative intensity | |
| differentiation-associated Na-dependent inorganic phosphate cotransporter | Hs.242821 | 4.61E−06 | 242 ± 143 | 0.015 ± 0.009 | 529 ± 238 | 0.040 ± 0.018 | 0.46 |
| Consensus: regulator of G-proten signalling 4 | Hs.227571 | 2.56E−07 | 1,875 ± 834 | 0.116 ± 0.052 | 4,087 ± 1,698 | 0.308 ± 0.128 | 0.46 |
| Consensus: hypothetical protein FLJ10649 | Hs.8768 | 2.13E−06 | 708 ± 285 | 0.044 ± 0.018 | 1,511 ± 681 | 0.114 ± 0.051 | 0.47 |
| KIAA0985 protein | Hs.21239 | 3.13E−05 | 742 ± 338 | 0.046 ± 0.021 | 1,422 ± 387 | 0.107 ± 0.029 | 0.52 |
| Wnt inhibitory factor-I | Hs.284122 | 8.43E−05 | 330 ± 143 | 0.020 ± 0.009 | 621 ± 291 | 0.047 ± 0.022 | 0.53 |
| calcium channel, voltage-dependent, gamma-subunit 3 | Hs.7235 | 1.05E−04 | 619 ± 344 | 0.038 ± 0.021 | 1,143 ± 526 | 0.086 ± 0.040 | 0.54 |
| Consensus: neurofilament, light polypeptide (68 kD) | Hs.211584 | 4.09E−04 | 2,292 ± 1,524 | 0.142 ± 0.095 | 4,205 ± 1,863 | 0.317 ± 0.140 | 0.55 |
| Consensus: hypothetical protein | Hs.302689 | 5.41E−05 | 4,188 ± 2,003 | 0.260 ± 0.124 | 7,577 ± 3,050 | 0.570 ± 0.230 | 0.55 |
| Consensus: somatostatin | Hs.12409 | 6.21E−04 | 535 ± 450 | 0.033 ± 0.028 | 966 ± 344 | 0.073 ± 0.026 | 0.55 |
| potassium voltage-gated channel, subfamily F, member 1 (KCNF1) | Hs.23735 | 8.44E−03 | 292 ± 200 | 0.018 ± 0.012 | 522 ± 377 | 0.039 ± 0.028 | 0.56 |
| Consensus: mRNA for C11ORF25 gene | Hs.91791 | 7.28E−06 | 770 ± 247 | 0.048 ± 0.015 | 1,378 ± 571 | 0.104 ± 0.043 | 0.56 |
| visinin-like protein 1 | Hs.2288 | 1.68E−04 | 6,337 ± 2,748 | 0.393 ± 0.170 | 11,282 ± 4,093 | 0.849 ± 0.308 | 0.56 |
| Consensus: MADS box transcription enhancer factor2 | Hs.78995 | 4.97E−05 | 1,553 ± 610 | 0.096 ± 0.038 | 2,762 ± 1,243 | 0.208 ± 0.094 | 0.56 |
| regulator of G-protein signalling 4 | Hs.227571 | 1.00E−03 | 576 ± 229 | 0.036 ± 0.014 | 1,006 ± 583 | 0.076 ± 0.044 | 0.57 |
| Kalirin (huntingtin-associated protein interacting protein) | Hs.8004 | 1.17E−07 | 843 ± 255 | 0.052 ± 0.016 | 1,432 ± 389 | 0.108 ± 0.029 | 0.59 |

TABLE III

Demongraphy and ApoE Brain Samples

| | Sex (sample number) | Age | PMI | Brain Weight (g) | ApoE Type | | | | |
|---|---|---|---|---|---|---|---|---|---|
| | | | | | E3/E2 | E3/E3 | E4/E3 | E4/E4 | E4/E2 |
| AD | Female (10) | 78 ± 6.2 | 3.2 ± 1.0 | 1,061.9 ± 167.4 | 0 | 2 | 4 | 3 | 1 |
| | Male (9) | 82 ± 7.6 | 3.0 ± 0.7 | 1,203.3 ± 126.8 | 0 | 1 | 7 | 1 | 0 |
| Control | Female (7) | 85 ± 9.1 | 3.0 ± 0.8 | 1,085.7 ± 70.5 | 0 | 5 | 2 | 0 | 0 |
| | Male (8) | 85 ± 9.0 | 2.4 ± 0.7 | 1,255.0 ± 75.5 | 1 | 5 | 2 | 0 | 0 |

TABLE IV

Top 15 Over-expressed genes in AD cerebella.

| Gene Name | Unigene | p value | AD cerebellum | | Control cerebellum | | AD/C |
|---|---|---|---|---|---|---|---|
| | | | Intensity | Relative intensity | Intensity | Relative intensity | |
| hypothetical protein FLJ21148 | Hs.193300 | 1.85E−03 | 620 ± 341 | 0.057 ± 0.031 | 353 ± 123 | 0.031 ± 0.011 | 1.76 |
| Consensus: methionine-tRNA synthetase | Hs.279946 | 8.71E−04 | 642 ± 306 | 0.059 ± 0.028 | 382 ± 92 | 0.033 ± 0.008 | 1.68 |
| hypothetical protein Telethon_Strait02270_FL142 | Hs.273186 | 1.32E−03 | 2,699 ± 1,356 | 0.249 ± 0.125 | 1,651 ± 453 | 0.144 ± 0.040 | 1.63 |
| inositol hexakisphosphate kinase 2 | Hs.323432 | 2.82E−03 | 2,605 ± 1,383 | 0.240 ± 0.128 | 1,601 ± 493 | 0.140 ± 0.043 | 1.63 |
| Homo sapiens KIAA0408 gene product | Hs.118744 | 1.60E−03 | 531 ± 215 | 0.049 ± 0.020 | 337 ± 101 | 0.029 ± 0.009 | 1.58 |
| Consensus: RNA binding motif protein 10 | Hs.154583 | 7.43E−03 | 1,382 ± 699 | 0.128 ± 0.064 | 894 ± 297 | 0.078 ± 0.026 | 1.55 |
| Consensus: ESTs | Hs.227170 | 5.16E−03 | 1,149 ± 552 | 0.106 ± 0.051 | 749 ± 249 | 0.066 ± 0.022 | 1.53 |
| Homo sapiens KIAA0445 gene product | Hs.301055 | 5.86E−03 | 769 ± 337 | 0.071 ± 0.031 | 512 ± 199 | 0.045 ± 0.017 | 1.50 |
| Consensus: hypothetical C2H2 zinc finger protein | Hs.165983 | 9.33E−03 | 624 ± 257 | 0.058 ± 0.024 | 415 ± 201 | 0.036 ± 0.018 | 1.50 |
| hypothetical protein FLJ10199 | Hs.30925 | 1.35E−03 | 620 ± 223 | 0.057 ± 0.021 | 419 ± 97 | 0.037 ± 0.009 | 1.48 |
| Cadherin | Hs.55173 | 6.22E−04 | 685 ± 243 | 0.063 ± 0.022 | 466 ± 98 | 0.041 ± 0.009 | 1.47 |
| Consensus: KIAA0973 protein | Hs.227489 | 9.35E−03 | 849 ± 368 | 0.078 ± 0.034 | 587 ± 186 | 0.051 ± 0.016 | 1.45 |
| arachidorate 5-lipoxygenase | Hs.89499 | 3.30E−03 | 1,130 ± 431 | 0.104 ± 0.040 | 785 ± 231 | 0.069 ± 0.020 | 1.44 |
| hypothetical protein FLJ11939 | Hs.94229 | 8.40E−05 | 1,348 ± 299 | 0.124 ± 0.028 | 948 ± 194 | 0.083 ± 0.017 | 1.42 |
| Consensus: ESTs | Hs.6700 | 7.69E−04 | 731 ± 220 | 0.067 ± 0.020 | 519 ± 131 | 0.045 ± 0.011 | 1.41 |

TABLE V

Top 15 Under-expressed genes in AD cerebella.

| Gene Name | Unigene | p value | AD cerebellum | | Control cerebellum | | AD/C |
|---|---|---|---|---|---|---|---|
| | | | Intensity | Relative intensity | Intensity | Relative intensity | |
| Fork head-like protein | Hs.14845 | 3.22E−03 | 429 ± 360 | 0.040 ± 0.033 | 751 ± 360 | 0.066 ± 0.031 | 0.57 |
| Consensus: KIAA0679 protein | Hs.5734 | 4.96E−03 | 662 ± 468 | 0.080 ± 0.043 | 1,289 ± 429 | 0.113 ± 0.038 | 0.67 |
| fibroblast growth factor 14 | Hs.197757 | 7.76E−03 | 606 ± 386 | 0.056 ± 0.036 | 902 ± 301 | 0.079 ± 0.026 | 0.67 |
| gephyrin | Hs.13405 | 8.67E−03 | 427 ± 240 | 0.039 ± 0.022 | 833 ± 221 | 0.055 ± 0.019 | 0.67 |
| Non-POU-domain-containing, octamer-binding | Hs.172207 | 5.05E−03 | 651 ± 312 | 0.060 ± 0.029 | 959 ± 375 | 0.084 ± 0.033 | 0.68 |
| regulator of G-protein signaling 11 | Hs.65756 | 8.84E−03 | 437 ± 301 | 0.040 ± 0.028 | 644 ± 160 | 0.056 ± 0.014 | 0.68 |
| Consensus: myxoid liposarcoma specimens | Hs.99969 | 5.40E−03 | 486 ± 209 | 0.045 ± 0.019 | 713 ± 286 | 0.062 ± 0.025 | 0.68 |
| phospholipase C, beta 4 (PLCB4) | Hs.283006 | 8.55E−03 | 431 ± 264 | 0.040 ± 0.024 | 627 ± 227 | 0.055 ± 0.020 | 0.69 |
| ADP-ribosylation factor binding protein GGA2 | Hs.155546 | 1.48E−03 | 525 ± 225 | 0.049 ± 0.021 | 763 ± 237 | 0.067 ± 0.021 | 0.69 |
| golgin-67 | Hs.182982 | 6.37E−03 | 2,860 ± 1,555 | 0.264 ± 0.153 | 4,135 ± 1,023 | 0.362 ± 0.090 | 0.69 |
| MDS024 protein | Hs.286122 | 1.01E−03 | 534 ± 212 | 0.049 ± 0.020 | 772 ± 192 | 0.068 ± 0.017 | 0.69 |
| Non-POU-domain-containing, octamer-binding | Hs.172207 | 2.68E−03 | 1,175 ± 586 | 0.108 ± 0.054 | 1,690 ± 450 | 0.148 ± 0.039 | 0.70 |
| protein phosphatase 2, regulatory subunit B | Hs.155079 | 5.23E−03 | 539 ± 105 | 0.050 ± 0.010 | 755 ± 200 | 0.066 ± 0.017 | 0.71 |
| Cytochrome P450 retnoid metabolizing protein | Hs.91546 | 4.21E−03 | 631 ± 279 | 0.058 ± 0.026 | 881 ± 197 | 0.077 ± 0.017 | 0.72 |
| putative dimethyladenosine transferase | Hs.125819 | 7.27E−03 | 406 ± 127 | 0.038 ± 0.012 | 562 ± 94 | 0.049 ± 0.008 | 0.72 |

TABLE VI

Top 15 constantly expressed genes in AD and control hippocampi.

| Gene Name | Unigene | AD hippocampus | | Control hippocampus | |
|---|---|---|---|---|---|
| | | Intensity | Relative intensity | Intensity | Relative intensity |
| ribosomal protein L41 (RPL41) | Hs.324406 | 21,644 ± 8,112 | 1.76 ± 0.66 | 21,608 ± 9,431 | 1.58 ± 0.69 |
| Consensus: prostaglandin D2 synthase (21 kD, brain) | Hs.8272 | 16,188 ± 3,657 | 1.32 ± 0.30 | 16,260 ± 3,899 | 1.19 ± 0.29 |
| ribosomal protein L3 (RPL3) | Hs.119596 | 15,854 ± 5,384 | 1.29 ± 0.44 | 15,744 ± 4,655 | 1.15 ± 0.34 |
| Consensus: clone TCBAP0774 | Hs.274472 | 9,842 ± 2,242 | 0.80 ± 0.18 | 9,816 ± 1,861 | 0.72 ± 0.14 |
| chaperone protein HSP90 beta | Hs.74335 | 8,787 ± 4,925 | 0.72 ± 0.40 | 6,780 ± 2,520 | 0.64 ± 0.18 |
| eukaryotic translation elongation factor 1 gamma | Hs.2166 | 8,475 ± 2,090 | 0.69 ± 0.17 | 8,515 ± 2,740 | 0.62 ± 0.20 |
| Consensus: ribosomal protein L22 | Hs.99914 | 8,118 ± 2,028 | 0.66 ± 0.17 | 8,151 ± 2,649 | 0.60 ± 0.19 |
| Consensus: ribosomal protein L17 | Hs.62202 | 7,605 ± 1,911 | 0.62 ± 0.16 | 7,636 ± 1,081 | 0.56 ± 0.08 |
| High-mobility group(nonhistone chromosomal) protein 1 | Hs.274472 | 5,321 ± 1,024 | 0.43 ± 0.08 | 5,322 ± 1,641 | 0.39 ± 0.12 |
| signal recognition particle 14 kD | Hs.180394 | 5,105 ± 911 | 0.42 ± 0.07 | 5,109 ± 840 | 0.37 ± 0.06 |
| ribosomal protein L44 | Hs.178391 | 4,963 ± 723 | 0.40 ± 0.06 | 4,981 ± 1,255 | 0.36 ± 0.09 |
| MM-1 beta | Hs.286856 | 4,895 ± 1,018 | 0.40 ± 0.06 | 4,901 ± 1,088 | 0.36 ± 0.08 |
| Consensus: cyclin 1 | Hs.79933 | 4,577 ± 1,151 | 0.37 ± 0.09 | 4,593 ± 1,070 | 0.34 ± 0.08 |
| Consensus: farnesyl-diphosphate farnesyltransferase 1 | Hs.48876 | 4,251 ± 949 | 0.35 ± 0.08 | 4,232 ± 1,929 | 0.31 ± 0.14 |
| Consensus: tetratricopeptide repeat domain 3 | Hs.118174 | 4,138 ± 1,490 | 0.34 ± 0.12 | 4,126 ± 1,412 | 0.30 ± 0.10 |

TABLE VII

Top 15 constantly expressed genes in AD and control cerebella.

| Gene Name | Unigene | AD cerebellum | | Control cerebellum | |
|---|---|---|---|---|---|
| | | Intensity | Relative intensity | Intensity | Relative intensity |
| ribosomal protein L3 | — | 17,103 ± 3,739 | 1.66 ± 0.36 | 17,111 ± 4,199 | 1.39 ± 0.34 |
| ribosomal protein L13a | Hs.119122 | 16,416 ± 3,932 | 1.60 ± 0.36 | 16,381 ± 3,340 | 1.33 ± 0.27 |
| Beta-actin | — | 13,049 ± 1,124 | 1.27 ± 0.11 | 13,102 ± 1,994 | 1.06 ± 0.16 |
| Similar to ribosomal protein S24 | Hs.180450 | 12,076 ± 1,278 | 1.17 ± 0.12 | 12,059 ± 1,582 | 0.96 ± 0.13 |
| actin, gamma 1 | Hs.14376 | 10,382 ± 1,610 | 1.01 ± 0.16 | 10,402 ± 908 | 0.84 ± 0.07 |
| syntaxin binding protein 1 | Hs.239356 | 9,279 ± 947 | 0.90 ± 0.09 | 9,308 ± 1,138 | 0.76 ± 0.09 |
| ribosomal protein S17 | Hs.5174 | 8,896 ± 2,120 | 0.87 ± 0.21 | 8,860 ± 1,159 | 0.72 ± 0.09 |
| hypothetical protein | Hs.8022 | 8,637 ± 1,927 | 0.84 ± 0.19 | 8,651 ± 2,432 | 0.70 ± 0.20 |
| KIAA0802 protein | Hs.27657 | 8,050 ± 1,111 | 0.78 ± 0.11 | 8,078 ± 1,490 | 0.66 ± 0.12 |
| Consensus: ribosomal protein S17 | Hs.5174 | 6,783 ± 1,613 | 0.66 ± 0.16 | 6,788 ± 1,209 | 0.66 ± 0.10 |
| fatty acid binding protein 7, brain | Hs.26770 | 6,703 ± 1,509 | 0.65 ± 0.15 | 6,733 ± 1,207 | 0.55 ± 0.10 |
| KIAA0275 gene | Hs.74583 | 6,038 ± 1,139 | 0.59 ± 0.11 | 6,058 ± 1,548 | 0.49 ± 0.13 |
| realin (RELN) | Hs.12246 | 5,944 ± 1,042 | 0.58 ± 0.10 | 5,958 ± 631 | 0.46 ± 0.05 |
| sortilin-related receptor, L(DLR class) A repeats-containing (SORL1) | Hs.278571 | 5,774 ± 1,122 | 0.56 ± 0.11 | 5,797 ± 990 | 0.47 ± 0.07 |
| cytochrome c oxidase subunit Vic | Hs.74649 | 5,623 ± 1,327 | 0.55 ± 0.13 | 5,626 ± 776 | 0.46 ± 0.06 |

Differential gene expression in AD cerebella, which is distinct from differential gene expression in AD hippocampi—Many genes were differentially expressed in AD and control cerebella (Tables IV-V). However, differences in AD versus control expression in cerebellum were statistically less significant than differentially expressed genes in hippocampus. Genes that were differentially expressed in AD cerebella were markedly different from the genes demonstrating differential expression in AD hippocampi.

Invariant genes—There were 433 genes with an AD/control ratio of ~1.0 in the hippocampi and 502 genes in the cerebella, demonstrating that these genes are not being differentially expressed. The top 15 genes are listed in Tables VI-VII, including several ribosomal proteins. GAPDH was also invariant with the AD/control ratio of 0.96 for the hippocampus and 0.93 for the cerebellum. β-actin was invariant but the AD/control ratios somewhat fluctuated between 1.0 and 0.8 depending on the gene chip probes. Also found to be invariant are other common housekeeping genes, such as GAPDH, β-actin, phosphoglycerate kinase 1, peptidylprolyly isomerase A, β$_2$-microglobulin, succinate dehydrogenase, transferrin receptor, aminolevulinate synthase, glucuronidase β, hydroxylmethyl-bilane synthase, hypoxanthine phosphoribosyltransferase β, tubulin β and TATA box binding protein.

Figure 1:
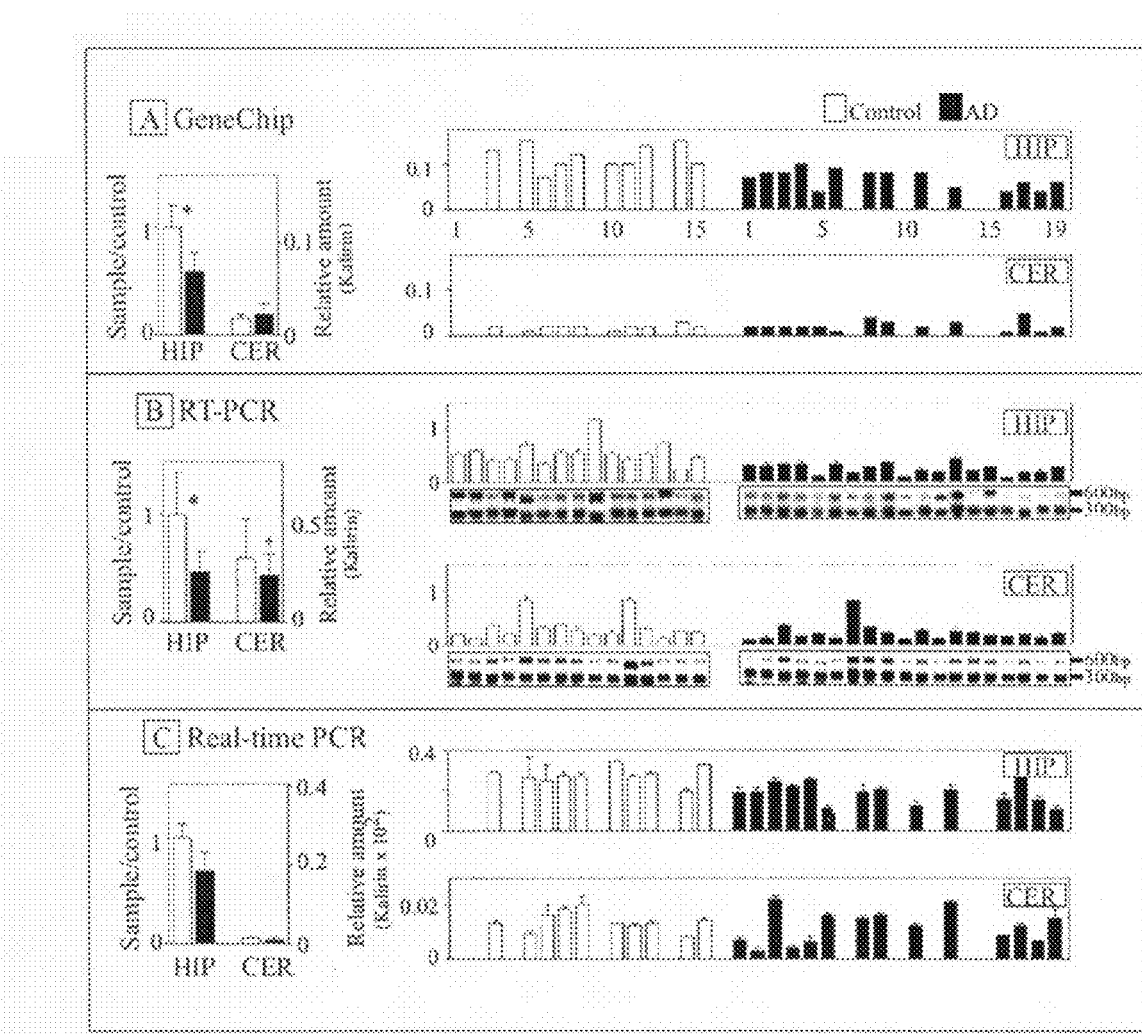
FIG. 1A-C shows expression of kalirin. Hippocampal and cerebellar specimens are numerically designated as AD 1-19 and control 1-15 throughout the figures and presented in the same order. (A) GeneChip analyses—the mean values of Kalirin, individual values of hippocampal specimens (HIP) and cerebellar specimens (CER). Open bars for control, black bars for AD. The left side "Y" axis represents the ratio of sample/control value, and the right side "Y" axis represents the actual value. The means (bars) and standard deviations (error bars) are presented. HIP=hippocampus and CER=cerebellum. The marked samples show statistically significant differences between AD and control. The samples with significant differences are marked as (*) for $p<0.0001$ and (+) for $0.05<P>0.0001$. Unmarked samples show no significant difference between AD and control. These formats are also used in all of FIGS. 1 and 2. (B) RT-PCR results presented the same as in (A). The upper gel bands represent Kalirin and the lower bands GAPDH. (C) Real time PCR results presented the same as in (A).
Figure 2:
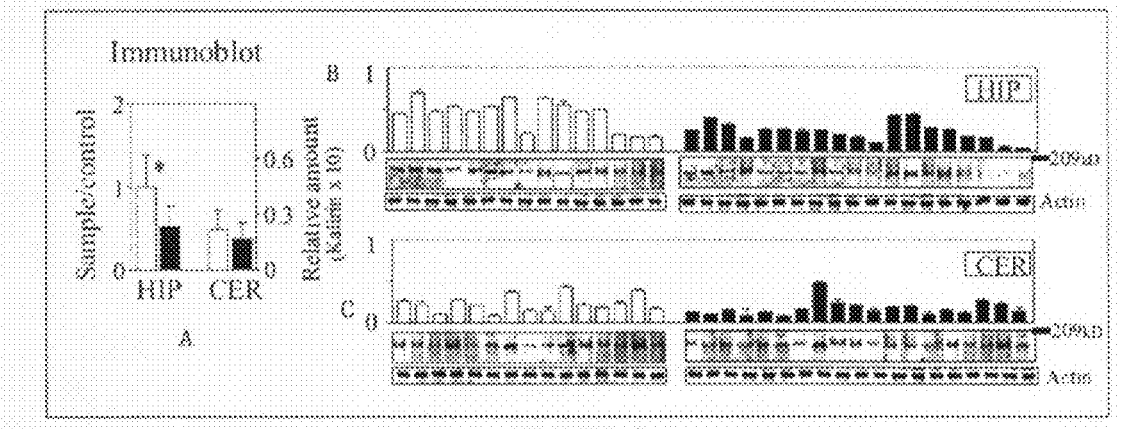
FIG. 2A-C shows immunoblots of Kalirin. An equal amount of solubilized proteins from individual specimens was electrophoresed and blotted for Kalirin (upper blots) and actin (lower blots). (A) the mean values, (B) values of individual hippocampal specimens and (C) values of individual cerebellar specimens as described in FIG. 1. The 209 kDa protein marker is indicated.

Kalirin-7 is markedly and consistently under-expressed in AD hippocampi—The gene with the highest statistical significance from the analysis was Kalirin, with a p-value of $1.17 \times 10^{-7}$. Remarkably, it was under-expressed in all of the AD hippocampal specimens compared to the control specimens, except one control hippocampal specimen (FIG. 1A). Kalirin's expression ratio of AD/control was 0.59, which is the 15$^{th}$ most under-expressed gene in the AD hippocampi (FIG. 1A and Table II). Kalirin under-expression was further confirmed by semi-quantitative RT-PCR (FIG. 1B) and real time PCR (FIG. 1C) in these samples. In addition to the under-expressed Kalirin mRNA level, immunoblots identified one form of Kalirin in question as Kalirin-7, the most abundant isoform in adult brain, and showed that the protein expression level for Kalirin-7 was lower in AD hippocampi than control hippocampi (FIG. 2A). The less abundant larger forms of Kalirin are not detected with the antibody used in this work. In contrast to hippocampus, Kalirin mRNA and protein levels in cerebella did not show significant difference between AD and control specimens (FIGS. 1 and 2).

More active iNOS in AD hippocampus—Kalirin-7 has a number of isoforms consisting of distinct domains, including a lipid binding domain, 9 spectrin like repeats, and a GEF domain. These domains likely interact with various proteins and regulate them, including peptidylglycine α-amidating monooxygenase, huntingtin-associated protein 1 and iNOS. Kalirin is known to inhibit iNOS by forming enzymatically inactive heterodimers with iNOS, in both cultured cells and mouse brain.

iNOS activity was significantly higher in the AD hippocampus than in the control hippocampus (FIG. 3A). For example, the average activity of iNOS was 2.9 fold higher with $p<0.0001$ in the AD hippocampus than in the control hippocampus (FIG. 3A). When the 15 control and 19 AD hippocampal samples were sorted in order of increasing iNOS activity (FIG. 3A), the AD hippocampi showed higher iNOS activity than control hippocampi. In contrast to hippocampus, the iNOS activity of control and AD cerebella was not significantly different from the control hippocampus value (FIG. 3A).

Expression of iNOS protein and mRNA in AD and control hippocampus—The increase in the iNOS activity could be due to either higher enzyme concentration or an intrinsically more active enzyme. The expression levels of the iNOS protein varied considerably among the individual hippocampal specimens, regardless of AD and control, and the average expression level of iNOS protein was not significantly different in AD than control (FIG. 3B). Similarly, individual hippocampal specimens showed notable variations, with the similar average mRNA level in AD and control. Taken together, the results indicate that the higher activity of iNOS in AD hippocampus is not related to expression levels.

Figure 4:
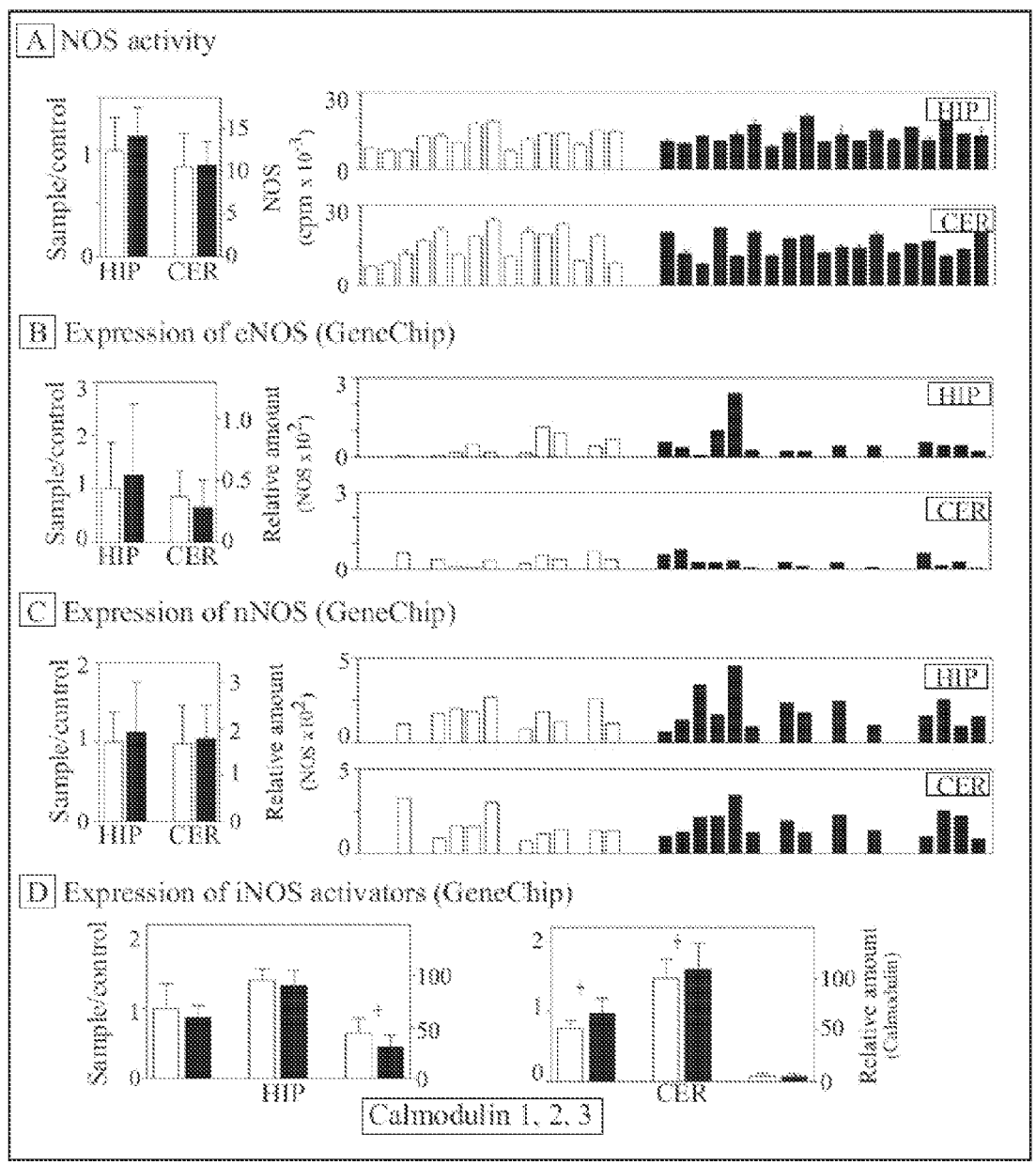
FIG. 4A-D shows activity and mRNA expression level of eNOS and nNOS. (A) NOS activities, (B) gene chip data for eNOS and (C) gene chip data for nNOS are presented as described in FIG. 3C. (D) The average expression levels of calmodulins, putative iNOS activators in the hippocampus in the left panel and those in the cerebellum in the right panel.

Activity and expression of eNOS and nNOS—NO is produced by NO synthases (NOS), and there are three major isozymes, neuronal NOS (nNOS, NOS1), endothelial NOS (eNOS, NOS3) and iNOS(NOS2). The higher iNOS activity in AD hippocampus raises the question whether eNOS and nNOS are more active in AD hippocampus. The collective activity of all NOS was the same in AD hippocampi as in control hippocampi, (FIG. 4A). However, the expression levels of eNOS and nNOS vary significantly among individual specimens, particularly among AD hippocampi (FIGS. 4B and 4C). Their average expression levels were not significantly different in AD hippocampi than the controls (FIGS. 4B and 4C and Table VII). Furthermore, the results suggest that the expression levels of NOS isoforms alone do not explain their activity. The higher activity of iNOS in AD hippocampi could be attributed to lower inhibitor or higher activator or both. Although little is known about the inhibitors and activators of iNOS in the human hippocampus, calmodulins are thought to activate iNOS in some tissues. However, they do not appear to be involved, because the mRNA levels of calmodulins are similar between AD and control hippocampi as well as between AD and control cerebella (FIG. 4D).

Interaction of Kalirin-7 and iNOS—AD hippocampi, control hippocampi, AD cerebella and control cerebella were solubilized in Triton X-100. An equal protein amount of the hippocampal samples and cerebellar samples was immunoprecipitated with anti-iNOS beads or anti-Kalirin beads. The precipitates were solubilized in SDS and electrophoresed, and the resulting gel was blotted and probed with anti-Kalirin, anti-iNOS or anti-Flag (FIG. 5A). Kalirin-7 was found in all of the anti-iNOS immunoprecipitates and conversely, iNOS was present in all of the anti-Kalirin immunoprecipitates. In contrast, several nonspecific antibodies did not stain the Kalirin and iNOS bands, indicating the specificity of anti-Kalirin and anti-iNOS. These results indicate that Kalirin-7 and iNOS are complexed in the human hippocampus and cerebellum.

However, it was unclear whether the co-immunoprecipitated Kalirin and iNOS is complexed in a cell or during solubilization of Kalirin from one cell and iNOS from another cell. To test these possibilities the cells expressing Kalirin and the cells expressing iNOS were combined, solubilized, immunoprecipitated with anti-Kalirin-beads or anti-iNOS beads, and immuno-blotted (FIG. 5B). The two proteins were coimmunoprecipitated only when both were coexpressed in a cell, but not when they were expressed in separate cells. The results show that Kalirin and iNOS were complexed in a cell prior to solubilization and that the complex did not take place during the solubilization and immunoprecipitation.

Although the results indicate the association of Kalirin with iNOS, it is not clear whether these two molecules are complexed together with or without other molecules. So supernatants of AD and control hippocampi (500 µg) were immunoprecipitated with anti-Kalirin beads. The precipitate was solubilized in nonionic detergent, radio-iodinated with $Na^{125}I$, and fractionated on a Sephadex G-150 column to remove free 125I-iodine. The fractions were solubilized in SDS under the reducing condition and electrophoresed (FIG. 5C). The radio-iodination labels Tyr residues exposed near the surface of proteins but not those sequestered. The autoradiography of the fractions shows that most of the radioactivity was eluted in a fraction consistent with a >300 kDa complex (s). The autoradiograph showed a major band of iNOS and a minor band of Kalirin. A simplest explanation is that Tyr residues of iNOS are largely accessible to the radio-iodination, significantly more than those of Kalirin, although the inputs and immunoprecipitates of Kalirin and iNOS are similar as shown in FIG. 5A and FIG. 5B. To better assess the protein composition of the tubes, an equal CPM of the tube samples was electrophoresed. The autoradiograph revealed bands of <100 kDa in addition to the iNOS and Kalirin-7 bands. The band profile of all of the tubes is similar, suggesting that the complex contains Kalirin-7, iNOS and other proteins. In addition, the immunoprecipitation data confirm that the level of Kalirin-7 is lower in the AD tissues than in the control tissues, whereas the level of iNOS is not significantly different. Furthermore, iNOS is associated with Kalirin more in control hippocampus than in AD hippocampus, although only a small fraction of either protein is involved in this type of interaction at any given time. These results are consistent with the previous observations of FIGS. 3 and 4.

LPS or transfection with iNOS plasmid induces iNOS activity: Kalirin attenuates iNOS activity in cell lines—The effect of Kalirin-7 on the iNOS activity was examined in four cell lines (FIG. 7). The cells were stably transfected with the zeocin resistant pcDNA4 vector carrying the Kalirin-7 cDNA or empty vector. The level of iNOS protein was then increased in each cell line by transfection with the Geneticin resistant pcDNA3 encoding iNOS, treatment with LPS, or LPS plus Aβ1-42. The data show that iNOS activity was always suppressed to basal levels in the presence of Kalirin-7, the specific iNOS inhibitor, Canavanine, or the general inhibitor of NOS, L-NAME. Importantly, Aβ1-42 augments iNOS activity induced by LPS treatment, and the augmented iNOS activity was also attenuated by Kalirin, Canavanine and L-NAME.

Attenuation of iNOS is dependent on the concentration of the Kalirin plasmid and Kalirin domain—It is possible that stably expressed or over-expressed Kalirin disrupted the protein processing of iNOS rather than directly inhibiting its enzyme activity. To test this possibility, the AtT-20 cell line stably expressing iNOS encoded in Geneticin resistant pcDNA3 was transiently transfected with increasing amounts of the zeocin resistant pcDNA4 Kalirin-7 vector (FIG. 6A). Zeocin is considerably harsher than Geneticin and kills most of the cells that were not transfected in 36 h. The surviving co-transfected cell lines expressed increasing concentrations of the Kalirin-7 protein. In parallel, increasing concentrations of iNOS were co-immunoprecipitated with Kalirin-7 by anti-Kalirin. As a result the iNOS activity decreased. To test the putative toxic effect of the increasing Kalirin-7 plasmid concentrations on cell health, the *Renilla* luciferase assay system (Promega) was used as a transfection reference. The Kalirin plasmid did not impair the synthesis and activity of *Renilla* luciferase (FIG. 6A, solid line).

Kalirin has multiple domains, consisting of a Sec14p-like putative lipid binding domain, nine spectrin-like repeats, tandem DH and pleckstrin homology (PH) domain as shown in FIG. 6B. AtT-20 cells stably expressing iNOS were transiently transfected with pcDNA4 carrying different domains of Kalirin 7 cDNA. iNOS activity was attenuated by one Kalirin domain (D2) consisting of the 354 amino acid $V^{506}$-$Q^{860}$ sequence (of SEQ ID NO:2) but not by other domains (FIG. 6C). It suggests that Kalirin specifically attenuated the iNOS activity, and a certain domain(s) of Kalirin was responsible for the suppression. To further define the regulatory site for iNOS, the 418 amino acid $D^{474}$-$Q^{891}$ sequence of Kalirin (SEQ ID NO:2) was divided into 19 overlapping sections, each consisting of 33 amino acids (FIG. 6D). When the AtT-20 cells stably expressing iNOS were transiently transfected with the various pcDNA4s carrying individual sections, D2 domain and the wild type Kalirin 7, iNOS was suppressed most effectively by section # 8 (FIG. 6E). The suppression of iNOS was dependent on the concentration of the Kalirin section 8 plasmid, but *Renilla* luciferase, the internal reference, was not (FIG. 6F). The expression levels of the fragments, D2 and Kalirin 7 were similar according to their immunoblots for the Flag epitope attached at their N-termini (FIG. 6E lower panel). These results indicate the sequence around $K^{617}$ AARHLEVRIQDFVRRVEQRKLLLDMSVSFHTH$^{649}$ (SEQ ID NO:13) is largely, but not exclusively, responsible for the iNOS inhibition and suggests that the peptide mimic alone is capable of the suppression. The results indicate that Kalirin 7, not AKalirin, is responsible for the inhibition.

```
                        SEQUENCE LISTING
SEQ ID NO: 1
ATGACGGACCGCTTCTGGGACCAGTGGTATCTCTGGTATCTCCGCTTGCTCCGGCTGCTGGATCGAGGGTCTTT

TCGGAATGATGGTTTGAAAGCTTCTGATGTCCTTCCTATCCTAAAGGAAAAGGTGGCCTTCGTGTCTGGGGGTC

GTGATAAGCGAGGCGGACCCATCCTGACCTTCCCTGCTCGCAGCAATCATGACAGAATAAGACAGGAAGACCTG

CGGAAACTCGTGACGTATTTGGCCAGCGTGCCAAGTGAGGACGTGTGCAAACGTGGCTTCACTGTCATCATCGA

CATGCGGGGCTCCAAGTGGGACCTCATCAAGCCCCTCCTCAAAACGCTGCAGGAAGCCTTTCCAGCTGAGATCC

ATGTGGCCCTCATCATTAAACCCGACAACTTCTGGCAGAAACAGAAGACCAACTTTGGCAGCTCCAAATTCATC

TTTGAGACGAGCATGGTATCTGTGGAGGGCCTCACAAAGCTGGTGGACCCCTCCCAGCTGACGGAGGAGTTTGA

TGGCTCCCTGGACTACAACCATGAGGAGTGGATCGAACTGCGGCTCTCCCTGGAGGAGTTCTTCAACAGCGCCG

TGCACCTGCTCTCGCGCCTCGAGGACCTCCAGGAGATGCTAGCCCGGAAGGAGTTTCCTGTGGATGTGGAGGGC

TCTCGGCGGCTCATTGACGAACACACACAGCTCAAGAAAAAGGTGCTGAAGGCCCCTGTGGAGGAGCTGGACCG

GGAGGGGCAGCGGCTGCTGCAGTGCATCCGCTGCAGCGACGGCTTCTCAGGACGCAACTGCATCCCGGGCAGTG

CTGACTTCCAGAGCCTGGTGCCCAAGATCACCAGTCTCCTGGACAAGCTGCACTCCACCCGGCAGCACCTGCAC

CAGATGTGGCACGTGCGCAAGCTCAAGCTGGACCAGTGCTTTCAGCTGCGGCTCTTCGAGCAGGATGCTGAGAA

GATGTTTGACTGGATAAGCCACAACAAGGAGTTATTCCTCCAGAGCCACACGGAGATCGGAGTCAGCTACCAGT

ACGCCCTTGACCTCCAGACGCAGCACAATCACTTTGCCATGAACTCCATGAATGCCTATGTCAACATCAACCGC

ATCATGTCCGTGGCTTCCCGCCTCTCTGAGGCCGGTCATTATGCCTCACAACAAATCAAGCAGATCTCCACCCA

GCTGGACCAGGAGTGGAAGAGCTTTGCTGCTGCCCTGGATGAACGCAGCACCATCCTCGCCATGTCTGCTGTGT

TCCACCAGAAGGCTGAGCAGTTCCTGTCGGGAGTGGATGCCTGGTGCAAGATGTGCAGTGAAGGTGGTCTGCCA

TCCGAGATGCAAGACCTAGAGCTGGCAATCCACCACCACCAGACCTTGTATGAGCAGGTGACCCAAGCCTACAC

AGAGGTCAGCCAGGATGGCAAAGCACTACTTGATGTGCTGCAGCGGCCCCTGAGCCCTGGGAACTCCGAATCCC

TCACGGCCACAGCCAACTACTCCAAGGCAGTGCACCAGGTGCTGGACGTGGTGCATGAGGTGTTACATCACCAG

CGACGGCTGGAGAGCATCTGGCAGCACCGCAAGGTGCGGCTCCACCAGCGGCTGCAGCTCTGCGTCTTCCAGCA

GGATGTACAGCAGGTGTTGGACTGGATTGAAAACCATGGTGAGGCCTTTCTCAGCAAACACACTGGAGTTGGGA

AGTCCCTACATCGAGCCCGGGCCCTGCAGAAGAGGCATGATGACTTTGAAGAGGTGGCTCAGAATACGTACACC

AATGCGGACAAGCTCCTAGAAGCAGCAGAGCAGTTGGCTCAGACGGGGGAATGTGACCCCGAGGAGATCTACAA
```

-continued

```
GGCAGCTCGACACCTGGAGGTGCGCATCCAAGACTTCGTGCGCAGGGTGGAGCAGCGGAAGCTTCTCCTGGACA
TGTCTGTTTCCTTCCACACACACACCAAAGAGTTGTGGACATGGATGGAAGACCTTCAGAAGGAGATGTTGGAG
GATGTCTGTGCAGATTCTGTGGATGCAGTCCAGGAACTGATCAAACAGTTCCAGCAGCAGCAGACCGCCACTCT
AGATGCCACACTCAATGTCATCAAGGAAGGCGAAGACCTTATCCAGCAGCTCAGGTCAGCGCCTCCCTCCCTCG
GGGAGCCCAGCGAGGCCAGGGACTCGGCTGTGTCCAACAACAAAACACCCCACAGCAGCTCCATCAGCCACATC
GAGTCGGTCCTGCAGCAGCTTGATGATGCCCAGGTGCAGATGGAGGAGCTGTTCCACGAGCGGAAGATCAAGCT
GGACATCTTCCTGCAACTGCGCATCTTTGAGCAGTACACCATCGAGGTGACAGCAGAGCTAGACGCCTGGAATG
AAGACTTGCTTCGGCAGATGAATGACTTCAACACAGAGGACCTAACCCTGGCAGAACAGCGGCTGCAGCGCCAC
ACAGAACGGAAGCTAGCCATGAACAACATGACCTTTGAGGTTATCCAGCAGGGACAGGATCTGCACCAGTACAT
CACGGAGGTCCAGGCATCAGGAATTGAGTTGATCTGTGAAAAAGACATTGATCTGGCAGCCCAGGTGCAAGAGT
TATTGGAATTTCTCCATGAGAAGCAGCATGAATTGGAGCTCAATGCAGAGCAGACTCATAAGCGGCTAGAGCAG
TGCCTCCAATTACGTCACCTCCAGGCTGAAGTCAAACAGGTTCTGGGATGGATCCGCAATGGAGAGTCAATGCT
CAACGCCAGCCTGGTCAATGCCAGCTCTTTGTCGGAAGCAGAGCAGCTGCAGCGGGAGCACGAGCAGTTCCAAC
TGGCCATCGAGTCCCTCTTTCATGCCACTTCCTTGCAGAAGACGCACCAGAGTGCCCTGCAGGTACAGCAGAAA
GCCGAGGTGCTGCTCCAGGCCGGCCACTACGATGCCGATGCCATCCGGGAATGTGCTGAGAAGGTGGCCCTCCA
CTGGCAGCAGCTCATGCTGAAGATGGAAGACCGGCTAAAATTGGTCAATGCCTCTGTGGCCTTTTACAAAACTT
CTGAACAGGTGTGTAGTGTCCTGGAGAGCTTAGAGCAAGAATACCGGAGAGATGAGGACTGGTGTGGTGGACGA
GATAAGCTGGGGCCAGCAGCAGAGATCGACCATGTCATTCCCCTCATCAGCAAACATTTGGAACAAAAGGAGGC
CTTTCTTAAGGCCTGCACCCTGGCTCGGCGGAATGCTGAGGTGTTTCTCAAGTACATCCACAGGAACAACGTCA
GCATGCCCAGTGTCGCCAGCCACACTCGGGGACCCGAGCAACAAGTGAAAGCCATCCTGAGTGAGCTCCTGCAG
AGGGAGAATCGCGTGCTGCATTTCTGGACCTTGAAGAAGCGGCGGTTAGACCAATGCCAGCAATATGTGGTGTT
CGAGCGCAGCGCTAAGCAGGCGCTTGACTGGATCCAAGAAACAGGTGAATTTTACCTCTCAACACATACCTCCA
CTGGAGAGACCACAGAGGAGACTCAGGAACTGCTGAAAGAATATGGGGAATTCAGGGTGCCTGCCAAGCAAACA
AAGGAGAAGGTGAAGCTTCTGATTCAGCTGGCCGATAGCTTTGTGGAAAAAGGCCACATTCATGCCACGGAGAT
AAGGAAATGGGTGACCACGGTGGACAAGCACTACAGAGATTTCTCCCTGAGGATGGGAAAGTACCGATACTCAC
TGGAGAAAGCCCTAGGAGTCAACACAGAGGATAATAAGGACCTGGAGCTGGATATTATCCCAGCAAGCCTTTCG
GATCGGGAGGTCAAGCTGCGGGACGCCAACCACGAAGTCAATGAAGAGAAGCGGAAGTCAGCCCGGAAGAAAGA
ATTTATTATGGCTGAACTACTCCAGACAGAGAAGGCTTATGTAAGGGATTTGCATGAGTGCTTAGAGACCTACC
TGTGGGAAATGACCAGTGGTGTGGAGGAGATCCCCCCTGGGATCCTCAATAAAGAGCATATCATCTTTGGCAAC
ATCCAAGAGATCTACGATTTCCATAACAACATCTTCCTCAAAGAGCTGGAGAAGTACGAGCAACTGCCTGAGGA
TGTGGGACACTGCTTTGTTACCTGGGCAGACAAATTTCAGATGTATGTCACCTACTGTAAAAACAAGCCTGATT
CCAACCAGCTTATCCTGGAGCATGCGGGCACCTTCTTTGATGAGATACAACAGCGGCATGGTCTGGCCAACTCC
ATCTCTTCCTACCTAATTAAGCCTGTCCAAAGGATCACCAAATATCAACTGCTCCTGAAGGAACTTTTAACTTG
CTGTGAAGAAGGGAAAGGGGAGCTCAAGGATGGCCTGGAGGTGATGCTCAGTGTCCCAAAGAAAGCCAATGATG
CCATGCATGTCAGCATGCTGGAAGGGTTCGACGAGAACCTGGATGTGCAGGGGAGTTGATTCTCCAGGATGCC
TTTCAAGTGTGGGACCCGAAGTCGCTGATCCGGAAGGGGCGGGAGCGGCACTTGTTCCTCTTTGAGATCTCCTT
GGTTTTTAGCAAGGAGATCAAAGATTCTTCAGGACACACGAAATATGTTTACAAGAACAAGCTACTGACCTCAG
AGCTGGGTGTGACCGAGCACGTGGAGGGCGATCCCTGCAAATTCGCCTTGTGGTCTGGGCGCACCCCATCCTCA
GACAATAAAACAGTGCTGAAAGCCTCCAACATTGAAACCAAGCAGGAGTGGATCAAGAACATTCGAGAAGTGAT
TCAAGAAAGGATCATTCACCTGAAAGGAGCTTTAAAGGAGCCACTTCAGCTCCCCAAAACACCAGCCAAACAGA
```

-continued

```
GGAACAATAGTAAGAGGGATGGAGTGGAGGATATTGACAGCCAGGGGGATGGGAGCAGCCAACCAGACACCATC

TCCATTGCTTCTAGGACCTCTCAGAACACAGTGGACAGTGACAAGGATGGCAACCTTGTTCCTCGGTGGCACCT

GGGACCTGGAGATCCTTTCTCCACTTACGTTTAG
```

```
                                                          SEQ ID NO: 2:
   1  MTDRFWDQWYLWYLRLLRLLDRGSFRNDGLKASDVLPILKEKVAFVSGGRDKRGGPILTF

61  PARSNHDRIRQEDLRKLVTYLASVPSEDVCKRGFTVIIDMRGSKWDLIKPLLKTLQEAFP

121  AEIHVALIIKPDNFWQKQTNFGSSKFIFETSMVSVEGLTKLVDPSQLTEEFDGSLDYNH

181  EEWIELRLSLEEFFNSAVHLLSRLEDLQEMLARKEFPVDVEGSRRLIDEHTQLKKKVLKA

241  PVEELDREGQRLLQCIRCSDGFSGRNCIPGSADFQSLVPKITSLLDKLHSTRQHLHQMWH
                     (SD 1 domain start site)
 301  VRKLKLDQCFQLRLFEQDAEKMFDWISHNKELFLQSHTEIGVSYQYALDLQTQHNHFAMN

361  SMNAYVNINRIMSVASRLSEAGHYASQQIKQISTQLDQEWKSFAAALDERSTILAMSAVF

421  HQKAEQFLSGVDAWCKMCSEGGLPSEMQDLELAIHHHQTLYEQVTQAYTEVSQDGKALLD

481  VLQRPLSPGNSESLTATANYSKAVHQVLDVVHEVLHHQRRLESIWQHRKVRLHQRLQLCV
                     (SD 2 domain start site)
 541  FQQDVQQVLDWIENHGEAFLSKHTGVGKSLHRARALQKRHDDFEEVAQNTYTNADKLLEA

601  AEQLAQTGECDPEEIYKAARHLEVRIQDFVRRVEQRKLLLDMSVSFHTHTKELWTWMEDL

661  QKEMLEDVCADSVDAVQELIKQFQQQQTATLDATLNVIKEGEDLIQQLRSAPPSLGEPSE

721  ARDSAVSNNKTPHSSSISHIESVLQQLDDAQVQMEELFHERKIKLDIFLQLRIFEQYTIE

781  VTAELDAWNEDLLRQMNDFNTEDLTLAEQRLQRHTERKLAMNNMTFEVIQQGQDLHQYIT

841  EVQASGIELICEKDIDLAAQVQELLEFLHEKQHELELNAEQTHKRLEQCLQLRHLQAEVK
                     (SD 3 domain start site)
 901  QVLGWIRNGESMLNASLVNASSLSEAEQLQREHEQFQLAIESLFHATSLQKTHQSALQVQ

961  QKAEVLLQAGHYDADAIRECAEKVALHWQQLMLKMEDRLKLVNASVAFYKTSEQVCSVLE

1021  SLEQEYRRDEDWCGGRDKLGPAAEIDHVIPLISKHLEQKEAFLKACTLARRNAEVFLKYI

1081  HRNNVSMPSVASHTRGPEQQVKAILSELLQRENRVLHFWTLKKRRLDQCQQYVVFERSAK
                     (SD 4 domain start site)
1141  QALDWIQETGEFYLSTHTSTGETTEETQELLKEYGEFRVPAKQTKEKVKLLIQLADSFVE

1201  KGHIHATEIRKWVTTVDKHYRDFSLRMGKYRYSLEKALGVNTEDNKDLELDIIPASLSDR

1261  EVKLRDANHEVNEEKRKSARKKEFIMAELLQTEKAYVRDLHECLETYLWEMTSGVEEIPP
                         (DH domain)
1321  GILNKEHIIFGNIQEIYDFHNNIFLKELEKYEQLPEDVGHCFVTWADKFQMYVTYCKNKP

1381  DSNQLILEHAGTFFDEIQQRHGLANSISSYLIKPVQRITKYQLLLKELLTCCEEGKGELK

1441  DGLEVMLSVPKKANDAMHVSMLEGFDENLDVQGELILQDAFQVWDPKSLIRKGRERHLFL
                                                 (PH domain)
1501  FEISLVFSKEIKDSSGHTKYVYKNKLLTSELGVTEHVEGDPCKFALWSGRTPSSDNKTVL

1561  KASNIETKQEWIKNIREVIQERIIHLKGALKEPLQLPKTPAKQRNNSKRDGVEDIDSQGD

1621  GSSQPDTISIASRTSQNTVDSDKDGNLVPRWHLGPDPFSTYV  1663
```

SD: Spectrin domain
DH: guanine nucleotide exchange factor domain
PH: phosphoinositide binding domain Although the invention has been described with reference to the EXAMPLES above, it should be understood that various modifications can be made without departing from the spirit of the invention. Accordingly, the invention is limited only by the following claims.

What is claimed is:

1. A method for suppressing inducible nitric oxide synthase activity in a cell comprising contacting said cell with an effective amount of a kalirin polypeptide wherein the kalirin polypeptide is selected from the group consisting of SEQ ID NO: 3 and residues 3-33 of SEQ ID NO: 3, wherein the polypeptide suppresses inducible nitric oxide synthase activity.

2. A method of inhibiting nitric oxide cytotoxicity comprising contacting a cell capable of producing nitric oxide with a biologically effective amount of a kalirin polypeptide wherein the kalirin polypeptide is selected from the group consisting of SEQ ID NO: 3, and residues 3-33 of SEQ ID NO: 3 wherein the polypeptide reduces inducible nitric oxide synthase activity.

3. The method of claim 2, wherein the polypeptide is formulated in a pharmaceutically acceptable vehicle.

* * * * *